(12) United States Patent
Sholem

(10) Patent No.: US 7,702,522 B1
(45) Date of Patent: Apr. 20, 2010

(54) METHOD AND APPARATUS FOR TRACKING THE RELATIVE VALUE OF MEDICAL SERVICES

(76) Inventor: Steven L. Sholem, 6121 N. 1st Ave., Phoenix, AZ (US) 85013

( * ) Notice: Subject to any disclaimer, the term of this patent is extended or adjusted under 35 U.S.C. 154(b) by 1574 days.

(21) Appl. No.: 09/653,384

(22) Filed: Sep. 1, 2000

(51) Int. Cl.
*G06Q 10/00* (2006.01)
(52) U.S. Cl. .................. 705/2; 705/3; 705/4; 705/38
(58) Field of Classification Search .............. 705/2, 705/3
See application file for complete search history.

(56) References Cited

U.S. PATENT DOCUMENTS

| | | | | |
|---|---|---|---|---|
| 4,491,725 | A * | 1/1985 | Pritchard | 705/2 |
| 4,667,292 | A * | 5/1987 | Mohlenbrock et al. | 705/2 |
| 4,722,055 | A * | 1/1988 | Roberts | 705/36 |
| 5,325,293 | A * | 6/1994 | Dorne | 705/2 |
| 5,359,509 | A * | 10/1994 | Little et al. | 705/2 |
| 5,471,382 | A * | 11/1995 | Tallman et al. | 600/300 |
| 5,550,734 | A * | 8/1996 | Tarter et al. | 705/2 |
| 5,557,514 | A * | 9/1996 | Seare et al. | 705/2 |
| 5,732,401 | A * | 3/1998 | Conway | 705/29 |
| 5,737,539 | A * | 4/1998 | Edelson et al. | 705/3 |
| 5,812,988 | A * | 9/1998 | Sandretto | 705/36 |
| 5,819,228 | A * | 10/1998 | Spiro | 705/2 |
| 5,845,253 | A * | 12/1998 | Rensimer et al. | 705/2 |
| 5,915,241 | A * | 6/1999 | Giannini | 705/2 |
| 5,918,208 | A * | 6/1999 | Javitt | 705/2 |
| 5,924,073 | A * | 7/1999 | Tyuluman et al. | 705/2 |
| 5,924,074 | A * | 7/1999 | Evans | 705/3 |
| 5,978,780 | A * | 11/1999 | Watson | 705/40 |
| 5,991,733 | A * | 11/1999 | Aleia et al. | 705/8 |

(Continued)

FOREIGN PATENT DOCUMENTS

EP    935208 A2 *  8/1999

(Continued)

OTHER PUBLICATIONS

Newhouse, Joseph, Elizabeth Sloss, Willard Manning Jr., Emmet Keeler, Risk adjustment for a children's capitation rate, Fall 1993, Health Care Financing Review, vol. 15, No. 1, p. 39(16), File 149 #01436869.*

(Continued)

*Primary Examiner*—Gerald J. O'Connor
*Assistant Examiner*—Lena Najarian
(74) *Attorney, Agent, or Firm*—Schmeiser, Olsen & Watts LLP

(57) ABSTRACT

Methods and apparatus for tracking and evaluating the relative value, such as the net present value, of medical services provided to patients associated with third party payors ("TPPs"). Under various embodiments of the present invention, the relative value of medical services is considered in evaluating whether to enter into an agreement with a TPP, whether to accept a new patient, when and for how long to schedule a patient appointment, and how long a physician should meet with the patient. Methods and apparatus for improving the efficiency of a medical office are also disclosed whereby a physician may more effectively supply a patient with relevant information and provide prescriptions, record billing information, order supplies, and collect payment for services provided. Methods and apparatus for improving security within a medical office and reducing employee fraud are also disclosed.

21 Claims, 9 Drawing Sheets

U.S. PATENT DOCUMENTS

| | | | |
|---|---|---|---|
| 6,009,402 A * | 12/1999 | Whitworth | 705/4 |
| 6,018,723 A * | 1/2000 | Siegel et al. | 705/38 |
| 6,044,351 A * | 3/2000 | Jones | 705/2 |
| 6,061,657 A * | 5/2000 | Whiting-O'Keefe | 705/2 |
| 6,112,986 A * | 9/2000 | Berger et al. | 235/380 |
| 6,202,053 B1 * | 3/2001 | Christiansen et al. | 705/38 |
| 6,283,761 B1 * | 9/2001 | Joao | 434/236 |
| 6,302,844 B1 * | 10/2001 | Walker et al. | 600/300 |
| 6,324,516 B1 * | 11/2001 | Shults et al. | 705/2 |
| 6,341,265 B1 * | 1/2002 | Provost et al. | 705/4 |
| 6,343,271 B1 * | 1/2002 | Peterson et al. | 705/4 |
| 6,381,576 B1 * | 4/2002 | Gilbert | 705/2 |
| 6,456,983 B1 * | 9/2002 | Keyes et al. | 705/36 |
| 6,484,144 B2 * | 11/2002 | Martin et al. | 705/2 |
| 2001/0020229 A1 * | 9/2001 | Lash | 705/3 |
| 2001/0039525 A1 * | 11/2001 | Messmer et al. | 705/36 |
| 2002/0013752 A1 * | 1/2002 | Johnson et al. | 705/36 |
| 2002/0019789 A1 * | 2/2002 | Ginsberg | 705/36 |
| 2002/0032584 A1 * | 3/2002 | Doctor et al. | 705/3 |
| 2002/0035484 A1 * | 3/2002 | McCormick | 705/2 |
| 2002/0049659 A1 * | 4/2002 | Johnson et al. | 705/37 |
| 2002/0055858 A1 * | 5/2002 | Jackson | 705/3 |

FOREIGN PATENT DOCUMENTS

| | | | |
|---|---|---|---|
| JP | 2000076326 A | * | 3/2000 |
| JP | 2001052059 A | * | 2/2001 |
| WO | WO 9941653 A2 | * | 8/1999 |

OTHER PUBLICATIONS

20 Secrets of Negotiating Managed Care Contracts, Managed Care Week, vol. 7, No. 24, Jun. 30, 1997, File 636 #03622335.*

Pinkerton Steven, David Holtgrave, The cost effectiveness of HIV prevention from a managed care perspective, Journal of Public Health Management and Practice, Jan. 1998, vol. 4, issue 1, pp. 59-67.*

Taheri P.A., Trauma services: a profit center?, Journal of the American College of Surgeons, 1999, File 73 #07643269.*

Shea, Dennis, Medicare physician referral patterns, Health services research, vol. 34, No. 1, p. 331, File 148 #10965162.*

Poppel, Barry, What is your practice worth?, New York State Dental Journal, Apr. 2000, pp. 28-31.*

National prescribing centre, MeRec Briefing, An introduction to health economic (part 1), Issue No. 13, Sep. 2000.*

Profitability based real-time decisioning, Credit risk modeling and decisioning, May 28-30, 2002, presentation by Vijay Desai and Terrence Barker, HNC Software.*

* cited by examiner

METHOD AND APPARATUS FOR TRACKING THE RELATIVE VALUE OF MEDICAL SERVICES

BACKGROUND OF THE INVENTION

1. Field of the Invention

The present invention relates generally to determining and tracking a relative value, such as the net present value, of services provided by medical practitioners and staff. More particularly, the present invention relates to coordinating and tracking medical services and related information, and evaluating managed care organization payment patterns for medical services to reduce medical practitioner losses from unpaid, partial-paid and late-paid services. The invention is an integral part of an overall process of providing medical services designed to minimize costs, and restructure medical offices to take advantage of information technologies, wireless systems, local area networks, wide area networks, and the Internet to reduce operating costs and maximize efficiency. The invention also relates to methods and apparatus for streamlining medical practices to more efficiently serve patients and improve physician profitability.

2. State of the Art

The conventional practice of medicine is the result of centuries of improvements in medical technology. Yet, even as medical technologies have improved, the foundation of the medical practice has remained the same. Patients schedule an appointment, are greeted when they arrive for their appointment, and then meet with one or more physicians or other medical services providers. Medical services providers evaluate each patient, diagnose any problems, and recommend tests, prescriptions and other medical procedures as necessary. The patient is then charged for the medical services provided.

Another recent aspect of medical practice relates to medical services providers' relationships with insurance companies, medical managed care organizations or other third party payors ("TPPs"). As used herein, the term "TPP" is intended to include any organization through which one or more patients receive medical services to be billed through a common payment manager which may pay all or a portion of the charges to a medical practice or facility. Examples of TPPs include, but are not limited to, insurance companies, health maintenance organizations ("HMOs"), physician-hospital organizations ("PHOs"), managed services organizations ("MSOs"), preferred provider organization ("PPOs"), various physician alliances, physician-hospital and physician-medical facility agreements, and Medicare, Medicaid or other indigent, uninsured or under-insured payor supplement organizations.

A TPP may enter into separate or joint agreements with physicians and other medical services providers. Then, through agreements with patients in exchange for risk-adjusted paid premiums to the TPP, the TPP pays all or part of a patient's medical expenses. The level of care (i.e. type of service, access to service, duration of service, type and amount of medication, etc.) is adjusted by the TPP to set premiums and determine profitability. Medical services providers, based on their agreements with a particular TPP, agree to charge no more than a specified rate for each type of medical service provided according to a predetermined fee schedule. In exchange for agreeing to the predetermined fee schedule, medical services providers are placed on the TPP's list of preferred providers, or some other list which may determine what portion of the allowable fees the TPP will pay and what, if any, portion of the allowable fees the patient will pay. Other TPPs may agree to pay for all or a portion of medical services regardless of which medical services provider the patient visits. As used herein, the term "medical services provider" is intended to include one or more medical practitioners of any medical field or specialty which may have an opportunity to bill for medical services provided through a TPP. The term "medical services provider" specifically includes, but is not limited to, physicians in any medical field or specialty, nurses, medical assistants and other medical staff such as medical administration and counseling, and any offices, groups or groups of associated offices employing one or more physicians, independent medical contractors, nursing facilities, long and short-term care facilities, off-site providers (home care providers), occupational and physical therapists, behavioral health providers and ambulatory care facilities.

TPPs are formed as for profit businesses and generate profits from coordinating the delivery of medical care and there are benefits to medical service providers who sign agreements with TPPs. Particularly in more recent years, however, medical services providers who charge for services through TPPs have experienced problems.

One of the problems experienced by medical services providers is that TPPs have intentionally rationed parts of the health care delivery system to minimize costs and maximize profit. Examples of TPP rationing include: limiting allowable services, limiting access to medical care, increasing patient premiums, increasing the patient responsibility portion of medical costs, reducing allowable fees for providing medical services, increasing physician liability, decreasing, delaying or refusing payment to medical services providers, and driving up the costs of medical services providers who attempt to claim outstanding unpaid or partially paid claims. These "adjustments" to the process of compensating medical services has the net effect of reducing physician income. The United States Consumer Price Index (CPI) has steadily increased at the rate of 2% to 3% per year since 1994. Nevertheless, physician net income has steadily decreased from a 2.4% increase in 1994 to a 5.8% decrease in 1997. Studies show that physicians are working longer hours, face increasing liability, and have experienced a significant drop in job satisfaction.

Attempts have been made to increase provider income by streamlining medical practices through medical management systems. FIG. 1 illustrates a flow diagram of a conventional medical services process such as that employed by a medical services provider dealing with a TPP. For many TPP plans, prior to visiting a specialist, a referral from a primary care practitioner is required. The primary care physician must request permission for a referral from the TPP. The TPP must then issue a formal approval for a referral to the requesting physician/service provider. The authorization must also be in the specialists' office prior to a patient's visit to the specialist. Many authorizations state that the TPP's approval does not guarantee payment. Without the formal approval, however, no payment will be made to the specialist for medical services provided. More than 98% of referral requests are eventually approved, but the wait to obtain an approval may extend several weeks. The result of such approval requirements may significantly delay the delivery of health care, potentially harm the patient, and delay compensation for the medical services provided.

With a proper referral 2, if required, authorization 4 from the TPP for the medical services requested must be obtained. Conventionally, authorization 4 is accomplished by a medical services provider staff member contacting the TPP by phone or facsimile to exchange information regarding a patient requesting medical services. The exchanged information typically includes such information as the TPP plan with which the patient is associated, the type of services requested, and the name of the medical services provider who will provide the services. The TPP may refuse authorization or automatically authorize specified services, such as routine physician visits, based on the contract terms.

Once authorization 4 is granted, or in conjunction therewith, a patient's demographics 6 are recorded in the patient's records. To record a patient's demographics, conventionally, a patient completes a form including such information as the patient's name, addresses, relevant numbers, guarantor, employer or TPP information, summary of medical history, allergies, and the like. Once all or part of a patient's demographics are recorded 6, or in conjunction therewith, the patient is scheduled 8 for an appointment. The decision of when to schedule a patient for an appointment conventionally involves such factors as: the type of services requested, medical services provider availability, medical office resources availability and patient condition urgency. After an appointment is scheduled 8, the patient's relevant medical records are retrieved 10 prior to the patient's appointment.

At the time of the patient's appointment, the patient is welcomed by medical office staff and signs-in 12. Sign-in 12 signals to the medical staff that the patient has arrived, and typically also involves collecting a co-pay amount from the patient. The exact amount of the co-pay, whatever it may be, must be determined and collected prior to providing medical services. Co-pay amounts vary considerably and can fluctuate without warning. Sign-in 12, however, may also involve a more detailed record by the patient of the patient's medical history, a description of symptoms, or other patient demographics as needed. Various medical services providers request and retrieve different information from patients at different times throughout the process of providing medical services. When a patient's turn to be seen has arrived, the patient is conventionally greeted by a nurse or medical assistant who confirms basic patient information such as name, address, insurer and purpose of visit, and prepares the patient to be seen by the primary medical services provider, such as a physician or a nurse practitioner, for example by checking the patient's weight, blood pressure, pulse, medications, etc.

The patient is then seen by a primary medical services provider 16, such as a physician, who evaluates the present complaints of the patient or otherwise responds to the purpose for the patient visit, such as by performing a routine physical, the primary medical services provider diagnoses any problems found during the examination, recommends any treatment for problems found, prescribes any medications, procedures, tests, surgery, or the like, and explains the patient's condition to the patient. Either simultaneously with or subsequent to meeting with the patient, the primary medical services provider either dictates for later transcription, or otherwise records a report to the file describing the examination, diagnosis, recommendations for treatment, prescriptions and the like. A copy of the report is generated, signed and sent to the referring entity as well as being filed in the patient's records.

Following the patient's visit, the medical services provider bills 18 the patient, either directly or through the patient's TPP. Completed medical services are typically "checked-off" on a printed form and sent to a data entry clerk to enter diagnoses, codes and "list" prices into the existing office accounting system. Charges are forwarded to the TPP at the billing clerk's convenience. Once the TPP receives the charges, they are reviewed and eventually paid according to the rules and policies of the TPP who may pay according to their fee schedules on a time frame based on their cash flow requirements. Each office independently verifies payment accuracy and follows-up on late payments or non-payments. Gross charges are posted to a traditional accounts receivable system. Payments, discounts and write-offs are entered as received in the "explanation of benefits." The operation of medical services providers, including the details of the process as illustrated in FIG. 1, is well known to those of ordinary skill in the art.

One example of a company which provides computer systems to assist in managing medical services is Datamedic Corporation of Massachusetts. Datamedic offers software/hardware packages for patient scheduling, billing, claims processing and collections. In particular, Datamedic's PMstation system operates from the medical services provider's in-house computer server and may be used in any Windows®-based system. The PMstation system assists in coordinating multiple resources for a single patient visit such as a physician, nurse, examination room, examining instruments, etc. Datamedic also sells CHARTnote and CHARTstation systems which integrate with the PMstation system to store codified data directly into a local patient database to eliminate the need to separately transcribe and record the information into the patient's file, to reduce paper records, and to more easily access patient records. The CHARTstation system also includes features such as: an autofax to immediately send a letter or report to a referring clinician, a full history of a patient's prior visits, allergies and laboratory results, patient record database search and electronic prescription writing capabilities, risk management alerts such as drug-to-drug and drug allergy warnings and automatic TPP codings for payment. The Datamedic systems may be accessed from any Windows NT/95 computer, including handheld, pen-based computers such as those from Fujitsu and Mitsubishi.

Another medical management computer system sold to medical services providers is that distributed by QuadraMED of San Rafael, Calif. The QuadraMED Affinity system focuses on centralizing clinical and financial data by providing a database of patient management information such as insurer, age, gender, contact information, visit schedules and chart location. The database of patient management information is centralized by providing access to it through the Internet via a secured Web browser, allowing medical services providers to retrieve real-time patient management information from any location with a connection to the Internet. The QuadraMED system also manages financial and clinical information and attempts to increase practice profitability by checking for and reducing redundant data entry and generating summary and detailed management reports on practice efficiency.

Yet another medical management computer system sold to medical services providers is that distributed by Healtheon/WebMD of Atlanta, Ga. The Healtheon/WebMD system integrates numerous sub-systems which include sub-systems to confirm and process referrals and authorization, submit and track insurance claims for collecting, order and check laboratory tests, distribute text-based and administration information across email, fax, mail, and retrieve patient information from a common patient database. One sub-system of the Healtheon/WebMD system permits medical services providers to access medical dictionaries, encyclopedias, databases and other literature electronically for research purposes. Another sub-system permits medical services providers to select a lab test, confirm patient eligibility based on insurance coverage and then submit the test request electronically. Medical services providers may also access individual completed test results through the Internet. Yet another sub-system of the Healtheon/WebMD system permits a medical services provider to generate medication prescriptions and refill medication prescriptions electronically. The prescription sub-system also provides a patient's medication history, drug reference information, clinical alerts and drug-drug interactions to both authorized medical services providers and to patients.

The Healtheon/WebMD system is a transaction-based system that improves the transfer and storage of data through the Internet. It does not specifically address physician cost/profitability, although it does speed-up many labor intensive transactions to make the physician and other health care entities more efficient.

Conventional medical management systems presently sold focus on accepting patient demographics, scheduling patient visits, and creating charges and submitting them to a TPP or other payor. While a number of systems are available, most concentrate on a traditional accounts receivable system. These systems do not attempt to track TPP payments, nor do they assist in more efficient time management based on a value of the medical services provided against the resources required to deliver those services.

Fee schedules may be provided by an insurer. Such fee schedules are independently produced by TPPs and may or may not be linked to "official" Medicare or other fee schedules. More importantly, however, the allowable fee schedule amounts have very little, if anything, to do with the actual value of the promise of future payment by a particular TPP to a medical services provider. Because each TPP has a different method, timing, and strategy for payment, has a different financial strength behind the promise of payment, and has a different risk of becoming insolvent before providing payment, each TPP's promise for payment does not actually have the same practical value.

A.M. Best Company of Oldwick, N.J., generates an annual listing of its ratings of insurance companies, each insurance company in the list having assigned thereto a rating based upon A.M. Best Company's opinion of the financial strength of each company and its ability to meet its financial obligations as of the date of the listing. Not all companies are listed, however, and the listings do not provide an indication of the payment methods and strategies employed by the insurance companies or rankings for those insurance companies who have requested their rankings not be listed. Furthermore, the A.M. Best Company's listing does not provide an indication of the future likelihood of payment, or whether the insurance company has a worsening cash flow at any point after the annual data is collected.

For many patients associated with TPPs, there is a patient co-pay required at the time of a visit with a medical services provider. The co-pay amount may be only $10 or $20, but for a medical services provider with several physicians, there may be a large amount of co-pay money at the end of a day. One problem sometimes experienced by medical services providers is employees stealing the co-pay money rather than placing it in the account where it belongs. To avoid being caught, the employees may adjust the data entry records to indicate that they money was paid and accounted for at a different time so that a daily accounting will not reveal the missing money. Eventually, the fact that money is missing may become apparent, but by that time it may be difficult to determine who made the changes, a significant amount of money may have been stolen, and the money may already be spent and practically uncollectable. Another problem sometimes experienced by medical services providers is employees mis-stating their hours worked. When medical employees work at less than ideal efficiency and/or mis-state hours worked, physician profits are affected and unnecessary staffing adjustments may be made to accommodate the sharply increased work-load created by managed care. Appropriate staffing levels for the workload, accurate time keeping and employee accountability must be maintained to control medical costs. Medical facility loss due to employee theft of time, supplies, and the like is commonly called "shrinkage."

Additionally, conventional medical management systems still include many redundant activities which may be improved upon to enable medical practitioners to more efficiently and effectively treat patients. Therefore, it is desirable to have a medical management system which intelligently schedules patient visits and evaluates the efficiency of a medical practice based on a more reliable measurement of the value of the patient's method of payment. It is further desirable to simplify medical practice activities to increase efficiency and decrease fraud losses and, therefore, increase profits for medical practitioners.

SUMMARY OF THE INVENTION

The present invention provides a medical management system which considers a relative value of services provided to patients by a medical services provider. As used herein, the term "relative value" is intended to include any estimated or actual value calculated as a function of an actual or estimated cost of collecting the value such as a time cost, resources cost, inflation cost, risk allowance cost or any other cost and/or a desired profit margin. In particular embodiments of the invention, the relative value of services is an estimated net present value ("NPV") of services for patients associated with a particular third party payor ("TPP"). The relative value of the services provided is evaluated when determining whether to accept a new patient, whether to enter into a medical services agreement with a TPP, whether to schedule an appointment and for how long the appointment should last, which resources to reserve for the appointment, and how long a particular medical services provider should spend with a patient at the time of the appointment. The NPV of services is essentially the value of the services calculated as if payment were received today. The NPV of services considered takes into account the payment patterns of a TPP including, but not limited to, how long from the time of service it takes to collect payment from the TPP, what the allowable charges of the TPP are, and what percentage of the allowable charges for a particular service the TPP typically pays. The NPV of services considered may also account for lost investment opportunities, inflation, and administrative costs in tracking and collecting the future payments. Other relative value amounts may include additional information in conjunction with the NPV for appropriate determinations. Other relative value amounts may be calculated as a function of the operating costs and administrative costs of a particular medical services provider, the break-even point for particular services, a desired profit margin, and the apparent stability of a TPP based on trends in the TPP's payment patterns.

In response to a request for a medical services provider to enter into an agreement with a TPP, accept a new patient, schedule an appointment, or visit with a patient, an indicator is generated to express the desirability of the action or otherwise indicate an estimated profitability or relative value of the requested action to the particular medical services provider. With the appropriate indicator available, a medical services provider may more appropriately and effectively make decisions on future actions which have an effect on the profitability of the medical services provider's business. It is also contemplated that the parameters of a particular agreement, appointment, or other action, such as the duration of an appointment, may be adjusted prior to the medical services provider agreeing to the action, to increase the likelihood that the action will be profitable for the medical services provider and to maximize the profitability of dealings with a particular TPP. In one specific embodiment, a primary medical personnel, such as a physician, is provided with a timer during a visit with a patient to indicate a recommended visit duration within which the physician may still "break-even", or more preferably make a profit, on the visit.

Corresponding software, hardware and interrelated systems enable the various embodiments and aspects of the present invention by storing TPP and statistically significant sampling of payment pattern histories and related data from a plurality of medical services providers in a common location to increase the usefulness of the information. According to embodiments of the present invention, at any time, a medical services provider may access appropriately configured software to generate a report on the real-time profitability of the medical services provider's business generally, or specifically, the profitability of relations with a particular TPP. The medical services provider may also generate graphs or other reports illustrating outstanding payments due by individual TPPs, how long the payments are overdue, and when payments are expected based on the payment patterns of the TPPs. It is further contemplated that by tracking the payment patterns of a TPP over time, and analyzing the payment pattern trends of a TPP, it may be predicted when a TPP is struggling financially and likely to become insolvent. The unique predictive ability of this system allows an early warning to medical services providers which reduces a TPP's ability to hide pending insolvency and allows medical services providers to better evaluate whether the TPP is attempting to receive medical services for their patients without the intention of properly compensating the medical services providers. In specific embodiments of the present invention, appropriately configured and accessible databases are available through the Internet to enable access to relevant data from any appropriately configured desktop, laptop or other personal computer having software for accessing the appropriate databases and performing the required calculations.

According to other aspects of the present invention, the medical management system includes time-saving and efficiency increasing devices and methods to increase the profitability of a medical services provider's business. According to one aspect, primary medical personnel are provided with remote access terminals such as wireless tablets for accessing patient records, recording patient evaluation and management information, and displaying and accessing information to assist in explaining a condition, medication, or the like, to a patient. The remote access terminals may also be used to allow the primary medical personnel to automatically order recommended reading materials through the Internet for delivery to the patient's home, send relevant information to the patient by email during the visit, and provide multimedia presentations to the patient. Billing for services is accomplished at the point of service via the Internet. According to another aspect, laboratory test results are accessible by an authorized medical personnel to display not only individual laboratory test results, but laboratory test result summaries and trends including graphs of changes in laboratory test results over time. According to yet another aspect of the present invention, primary medical personnel prescriptions may be automatically ordered and delivered to a patient's home from an indication by a physician on a patient's electronic medical record that a prescription should be issued. According to still another aspect, a primary medical personnel records a "superbill" on a remote access terminal during a patient's visit and automatically sends the "superbill" to the medical services provider's accounting software and to the TPP for payment upon completion of the patient's visit without the need for a data entry clerk.

According to yet other aspects of the present invention, the medical management system includes apparatus and methods to reduce fraud within a medical services provider's business by attaching biometric identification devices such as finger print, face print and retinal scanning devices to management system access terminals. By using biometric identification devices, employees' access to information may readily be controlled and monitored, and employees' use of computers may be monitored. In the case of a receptionist or data entry clerk, exact logon and logoff times may be identified for a specific employee for purposes of payment. In the case of an employee who receives copay payments from patients, specifically which employee received the payment may be tracked, and regular balance sheets to indicate the amount of money which should be in the drawer may be produced.

According to a specific aspect of the present invention, supply needs, use and ordering may also be tracked by the medical management system to determine, at any particular time, the expected number of a particular supply to be used before the next ordering period. Appropriately configured software may evaluate the existing number of a particular supply, the average number of that supply used within a typical ordering period, and whether there are more than an average number of appointments already scheduled which will use that particular supply. Through regular checking of supply inventory using bar code scanning and carefully tracking use of particular supplies, this method may also reduce theft of supplies and overall inventory.

BRIEF DESCRIPTION OF THE SEVERAL VIEWS OF THE DRAWINGS

The nature of the present invention as well as other embodiments of the present invention may be more clearly understood by reference to the following detailed description of the invention, to the appended claims, and to the drawings herein, wherein:

DETAILED DESCRIPTION OF THE INVENTION

The relative value of providing medical services to a patient may vary within a wide range of values for each of a variety of medical services providers. Additionally, as a function of the payment patterns of a variety of third party payors ("TPPs"), the relative value of providing the same medical service to a variety of patients having different TPPs may vary within a wide range of values. One example of a relative value calculation is the net present value ("NPV") of services. The concept of NPV relies, in part, on the principle that whenever services are performed in exchange for a promise of future payment, those providing the services are, in essence, granting a loan to those receiving the services until payment is made. In systems where billing for services is done periodically, such as for medical services, that loan is traditionally interest free if paid within a predetermined period. However, the value of a payment received at some point in the future is less than the value of the same payment received now. This decrease in value over time is due to numerous factors including, but not limited to, inflation, lost interest bearing investment opportunities (the time value of money), and administrative costs in tracking and collecting the future payment. Such calculations are well known in the art and may readily be performed by economists, accountants or financial analysts of ordinary skill in the art, using well-known equations.

Figure 1:
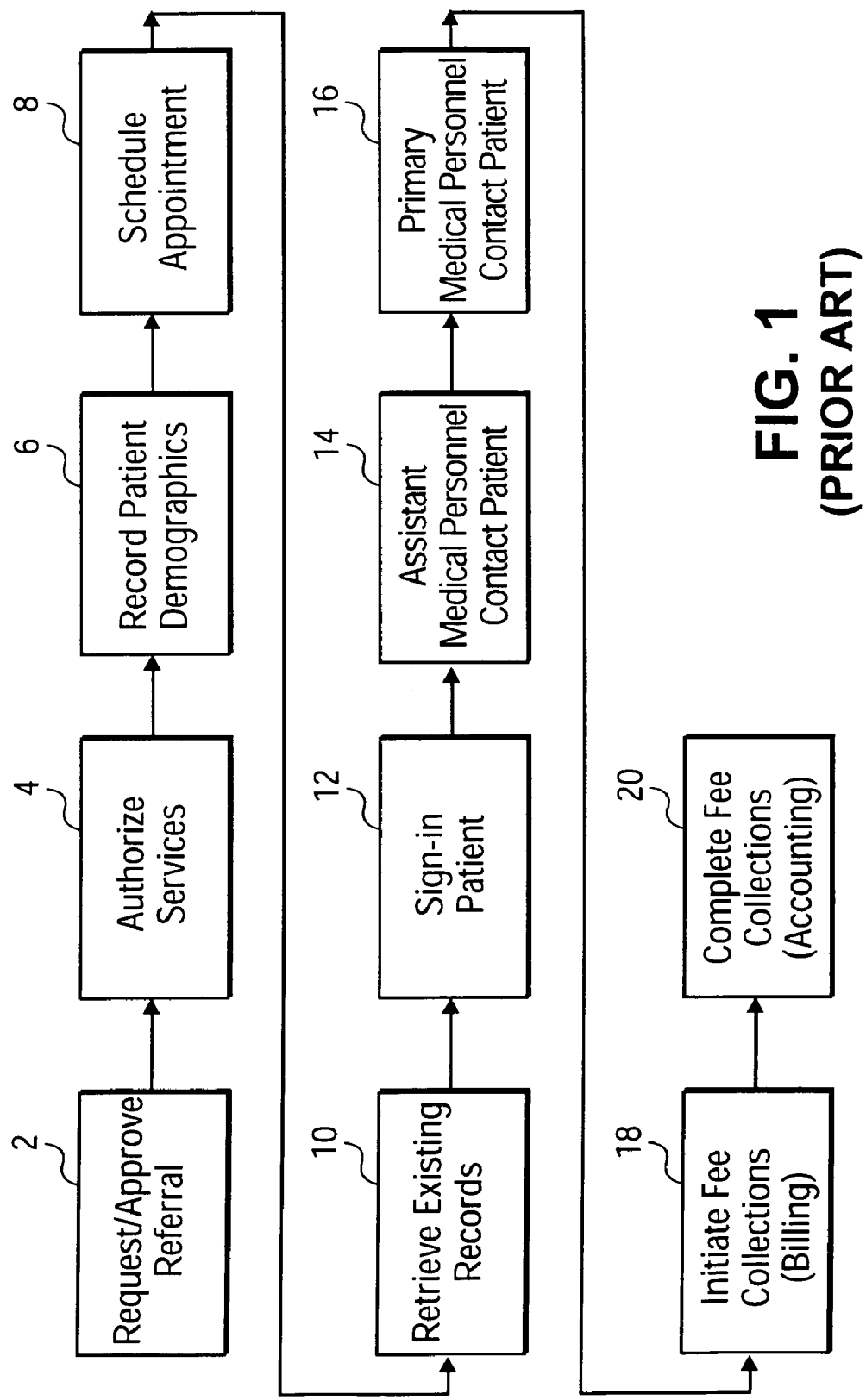
FIG. 1 includes a flow diagram of a prior art medical services process.
Figure 2:
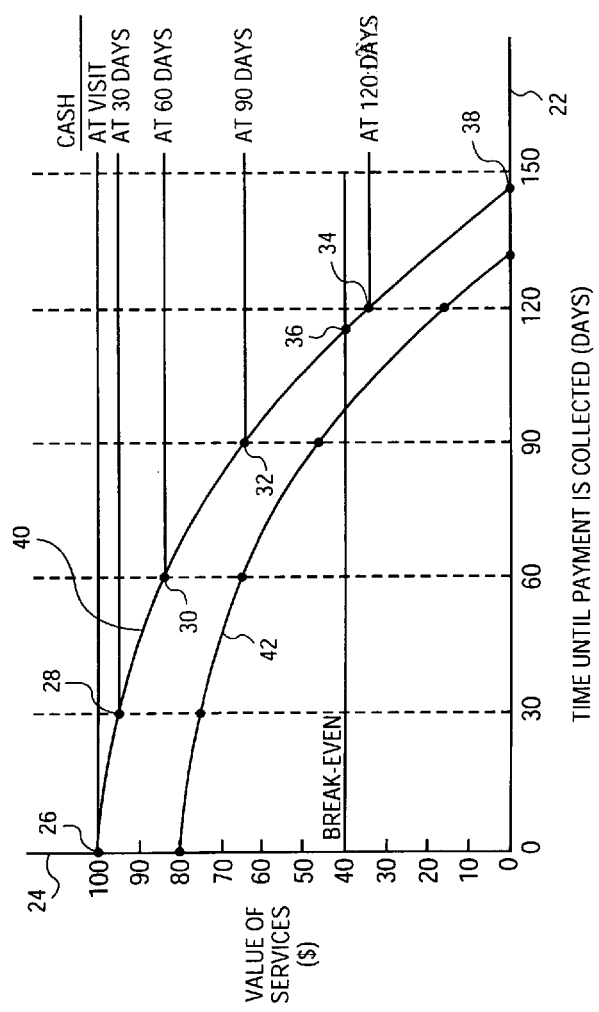
FIG. 2 includes a graph of the present value of medical services provided as a function of time until payment is collected.

FIG. 2 includes a graph illustrating how payment received at various times in the future may vary the value of the payment to a medical services provider at the time the services are provided. For the graph shown in FIG. 2, the horizontal axis 22 represents time which will pass until payment is collected for services provided today, and the vertical axis 24 represents the value of the services provided today calculated as if paid today. Points 26, 28, 30, 32, 34, 36 and 38 along the arcing line 40 represent the actual NPV of a medical service performed today as a function of when the payment for today's services will actually be collected. As illustrated by the first point 26, if medical services were provided today having a value of $100 and $100 cash was collected as payment at the time of service, the NPV of the $100 is $100. The $100 may be used immediately by the medical services provider for any purpose. If, however, payment is not collected for 30 days, the second point 28 on the arcing line 40, the NPV of the $100 services provided may only be $95. At the time the services are provided, the medical services provider is owed $100 for the resources and time expended to provide the services. Instead of immediately receiving $100, however, the medical services provider must wait 30 days. During those 30 days, inflation has decreased the buying power of the $100 dollars, the medical services provider has missed opportunities to invest the $100 in an interest bearing investment or has paid interest on outstanding debts which could have been paid by the $100, and the medical services provider has been required to expend resources to collect the $100 such as sending out a bill and tracking the status of the payment. In other words, under the present example, the $100 payment received in 30 days has the same value as a $95 payment received today.

As can be seen through the example provided in FIG. 2, the longer the delay before payment is collected, the lower the relative value of the payment to the medical services provider. Intuitively, this decrease is due to greater deflation of the value of money during the longer time, greater lost opportunities for alternative uses for the money, and greater administrative costs in collecting the money as time passes. For example, for a specific medical practice, a $100 payment received at 60 days, the third point 30, may have an NPV of $85, a payment received at 90 days, the fourth point 32, may have an NPV of $65, and a payment received at 120 days, the sixth point 34 on the arcing line 40, may have an NPV of $35. As also shown in the graph of FIG. 2, at some point 38, the NPV of the services will be $0. In other words, payment which will not be received until the sixth point 38 has no present value, and the medical services provider is essentially providing the services for free or at a loss. As should be clear to one of ordinary skill in the art, though readily determinable using well known equations, the actual path of the arcing line 40 for any specific time and medical service provider will vary because the specific characteristics of each service provider are different, and the relevant factors in a relative value calculation may vary over time.

Regardless of when payment is received, however, a medical services provider also incurs expenses by providing the medical services which must be paid. For example, the medical staff who performed the services and the other general office staff required to run a medical services provider office all need salaries and benefits, equipment used in providing the services must be purchased or otherwise paid for, cleaned and/or disposed of, the building in which the services were provided must be paid for, cleaned and updated, electricity and other utilities are needed, medical malpractice and other insurance must be paid, a profit margin is desirable, and many other expenses are required to make the medical services available. Thus, the medical services provider likely cannot afford to maintain the medical services for any significant length of time if the average relative value of payments is below the operating costs of the medical services provider's office. In other words, there is a break-even point 36 long before the NPV reaches $0, beyond which it is unprofitable for a medical services provider to provide services. Additionally, recent experience by medical services providers dealing with TPPs indicates that payment by some TPPs may be less than a full amount, and may require additional administrative expense to collect, thus, further affecting the relative value of the services to the medical services provider. The second arcing line 42 of the graph of FIG. 2 shows an instance where only 80% of the total bill is ever collected.

Because the various TPPs pay their bills differently, and on different payment schedules, some quickly paying their bills in full and others paying their bills late, only partially paying or not paying, it is more profitable for a medical services provider to provide services to those patients who are associated with TPPs which quickly pay their bills in full. By example, consider two medical services providers, each having a break even point of $40 on the arcing curve 40 of the graph of FIG. 2 and providing the same medical services for an average of 100 patients per week. The first medical services provider provides service only to patients of a first TPP which pays billed charges in-full at 30 days from service ($95/$100). The second medical services provider provides service only to patients of a second TPP, which uses the same allowable fee schedule as the first TPP, but which pays an average of 80% of the billed charges at 60 days from service ($66/$100). It should be clear from the graph shown in FIG. 2 that although both the first and second medical services providers are making a profit in their businesses and working for patients of TPPs with identical allowable fee schedules, the first medical services provider is making approximately $29 more profit today, on average, for each $100 in services billed when the NPV of the services is considered.

As illustrated by the previous example, the allowable fee schedule amounts of a TPP have very little to do with the present value of the promise of future payment by the TPP. Nevertheless, in conventional medical services management systems, the allowable fee schedule amounts of a TPP are a primary standard by which decisions to perform medical services are made. Conventional medical services management systems do not consider the relative value of medical services, the NPV or the relations between the relative value of medical services and the cost of operating a medical services provider's office in the determination of whether to accept a patient, how that patient should be scheduled or how much time that patient should be allotted for a visit.

According to a first aspect of the present invention, the relative value of potential medical services to be provided for a patient is calculated and considered as a factor in a determination of whether to accept a new patient or enter into an agreement with a new TPP. In one embodiment of this first aspect, when considering whether to accept a new patient, data relevant to the patient's TPP is reviewed and evaluated, and the TPP is assigned a rank, grade or other indicator to indicate to those considering whether to accept the new patient an estimated relative value of the likely services for the patient. It is contemplated that the rank assigned to the patient's TPP may be any rank form or style such as a color (e.g. red, yellow and green), a number or letter (e.g. 1 to 10 or A to F), a graded series of words (e.g. good, better and best), or more simply a brief indicator of acceptance or rejection (e.g. yes and no, or accept and reject). Although there are numerous factors which may be considered in evaluating data relevant to a TPP and generating a relative value of the services, such as an estimated NPV, and the factors to consider may vary for each application, relevant data may include, but are not limited to, one or more of: the average time for payment in general and for specific services; the average percentage of allowable billed charges paid, in general and/or for specific services; the allowable fees schedule; the number of patients associated with the TPP generally and within a particular region; the required copay amount for this or other patients; the total makeup of patient demographics for the specific services provider; activity-based costs involved in providing the medical services for a patient of the specific TPP; and the like. Preferably, data which is evaluated is regularly updated as additional charges are billed to and paid by TPPs. Most preferably, the data is maintained and updated in substantially real-time by an appropriate processor including software as described later herein. Based at least in part upon the rank assigned the patient's TPP, a decision-maker makes the decision of whether to accept the new patient. Of course, the decision-maker may be a medical services provider staff member, or may alternatively be an automated decision-maker such as a computer running appropriate software having an over-ride option for special circumstances.

In a second embodiment of the first aspect of the present invention, when considering whether to enter into an agreement with a new TPP, or to renew an agreement with a TPP, data relevant to the TPP and a relative value of the services provided to patients of the TPP, such as an NPV, is reviewed and evaluated and the TPP is assigned a rank, grade or other indicator, like with the first embodiment. Also similar to the first embodiment, the rank is based upon data relevant to the TPP and the decision to enter into the agreement is based upon at least a portion of the relevant data and/or the rank.

In other embodiments of the first aspect of the invention, in considering whether to enter into an agreement with a TPP or to accept a new patient, in addition to the data relevant to the TPP used in the first and second embodiments additional information is reviewed and evaluated in determining a relative value and/or a rank for consideration. As with the first and second embodiments of this first aspect, there are numerous other factors which may be considered, not all of which may be listed here. However, some significant data factors may include: data relevant to operation of the particular service provider considering the rank such as overall operating costs and overhead, specific costs for providing specific services, specific services offered by the service provider, accounts payable amounts, accounts receivable amounts, a desired profit margin and the like; and data more generally relevant to society such as an estimated or prevailing inflation rate, an estimated or actual investment interest rate, and the like.

According to a second aspect of the present invention, the relative value of medical services to be provided for a patient is calculated and considered as a factor in a determination of scheduling the patient for an appointment. In a first embodiment of the second aspect of the present invention, a rank for a patient, similar to the rank disclosed in the first aspect of the invention, is generated when a patient attempts to schedule an appointment. The rank is used by a scheduling employee of a medical services provider as a factor in determining when the patient will be scheduled for an appointment. Although there is a variety of data which may be used in generating the rank, not all of which may be practically listed here, the data may include such information as: the estimated NPV of the service requested by the patient for the TPP with which the patient associates; the estimated cost of providing that service; the operation costs of the specific service provider; a desired profit margin; the types of services being provided to other patients near similar appointment times; the urgency of the medical condition; the history of the patient with the services provider; and the like. For example, in a system where a ranking style of red, yellow and green is used, red may be used to indicate a low desirability of performance for the services requested by the patient and green to indicate a high desirability of performance for the services requested. In such a case, it may be determined that for red indicators, appointments should be scheduled at least one month away, but for green indicators, appointments should be scheduled as soon as possible within 1 or 2 days. Emergency appointments, of course, are seen in the traditional as-soon-as-possible fashion. However, retrospective analysis of the TPP's response to and appropriate payment for the patients seen on an emergency basis may form a decision basis for subsequent participation with that TPP. It is also contemplated that data relating to the specific periodic payment dates of a TPP may be considered in a determination of when to schedule a patient such that the patient may be scheduled most optimally near the closing date for the nearest payment cycle.

In a second embodiment of the second aspect of the invention, the relative value of medical services to be provided for a patient is used to determine the duration of a patient's appointment. When an appointment is scheduled, the recommended duration of the appointment may be adjusted for various relative value amounts, or considering other factors, to increase the likelihood that the visit will be profitable for the medical services provider. For example, if it is determined that the relative value of a requested medical service is $60 rather than the $100 billed for providing the services, the appointment may be scheduled for only 15 minutes instead of the typical 20 minutes to maintain the income required by, or desired by, the medical services provider's business. In this way, the medical services provider may more specifically analyze at the time of scheduling an appointment, from a history of transactions with a particular TPP, whether the medical services provider can provide the requested medical services at the required quality for the expected payment value.

In a third embodiment of the second aspect of the invention, a relative value of medical services to be provided for a patient is used to determine the scheduling of resources for a patient appointment. When an appointment is scheduled, associated resources such as office equipment, physicians, rooms, and support staff, are also scheduled to enable the medical services provider to completely provide the required services. In this third embodiment, the relative value of the medical service to be provided is considered in scheduling resources and the resources are each assigned a quality or desirability level such that the newest resources, most experienced physicians, largest rooms, etc. are scheduled for those patients associated with TPPs with high rankings, or for those medical services providing the greatest relative value. Although every medical services provider certainly desires to provide the best service and nicest resources to every patient, there are differences in resources even within an office. It may be advantageous to grant use of the best resources by those associated with TPPs who provide the greatest relative value for the medical services provider.

According to a third aspect of the present invention, a relative value of the medical services to be provided is considered by a physician, or other medical services provider employee, in determining the duration of time the physician should spend with a patient during an appointment. By specifically indicating the relative value, such as the NPV, of a particular medical service to the physician prior to the physician administering that service, the physician may better evaluate the length of time the physician should spend with that patient. Furthermore, if the physician knows the specific estimated time the physician should spend with the patient to make the visit profitable for the medical services provider, the physician may more efficiently visit with the patient to make the visit profitable. Certainly, however, the indicated time would only be a recommendation and the physician could adjust the actual time spent with a patient as required for a particular patient. In a particular embodiment, the physician, or other medical services provider employee, is provided with a time frame indicating the time remaining on the recommended visit time for a visit with a particular patient.

Figure 3:
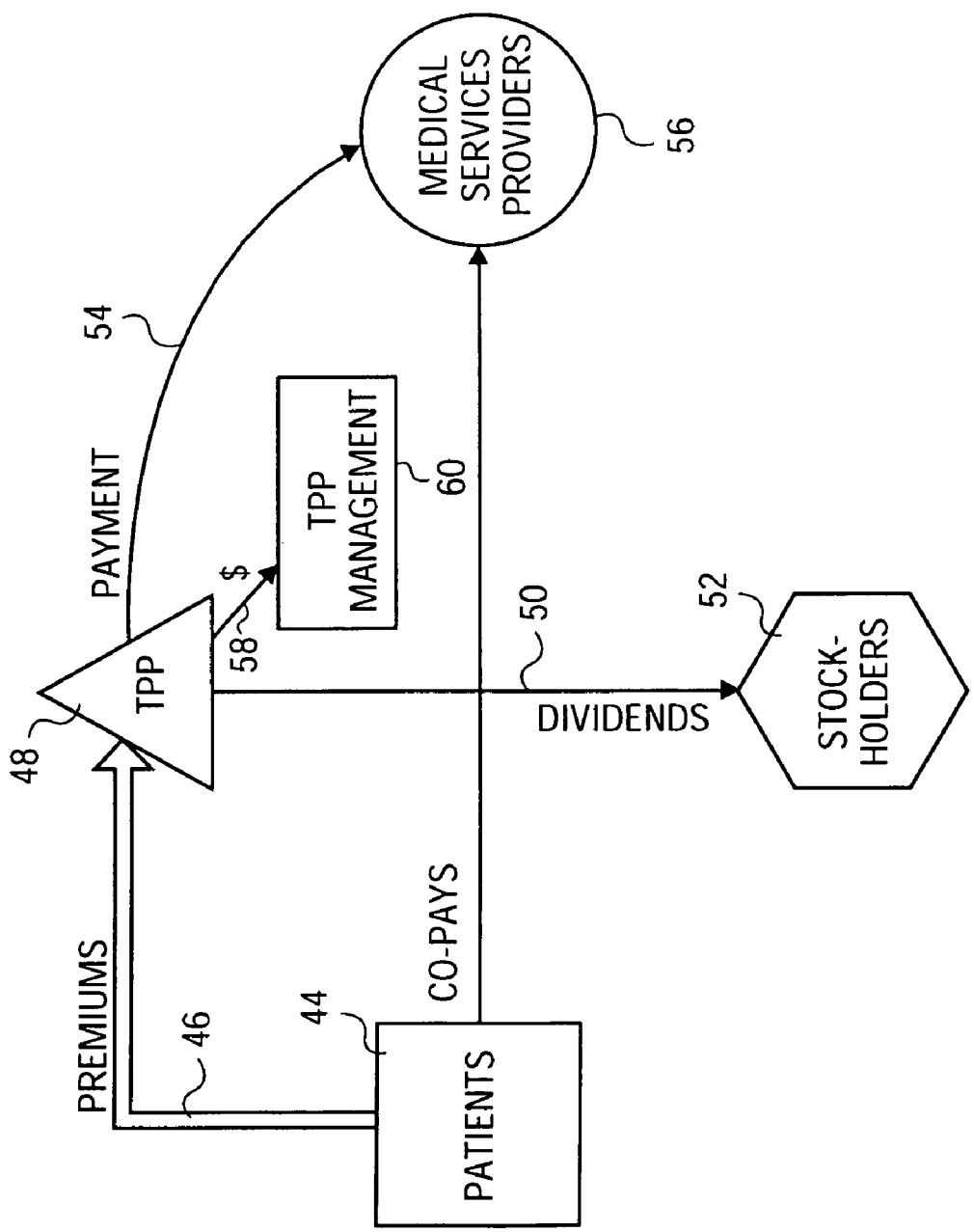
FIG. 3 includes a block diagram of the flow of money from patients to medical services providers.

According to a fourth aspect of the present invention, data relevant to a calculation of the NPV for medical services provided to patients of a particular TPP is used to predict the future insolvency of that TPP. TPPs are conventionally operated as a business for profit. As a business for profit, a primary concern of TPPs is the profitability of the business. Thus, when profit margins drop, TPPs find ways to bring those profits back up. As illustrated in the drawing of FIG. 3, patients 44 desiring medical services, or insurance for medical services payments, may pay premiums 46 to a TPP 48 in exchange for at least partial payment of future medical bills. With the money from the premiums, TPPs pay dividends 50 to their stockholders 52, money 58 in the form of salaries and bonuses to their management 60 and other employees, and pay 54 medical services providers 56 for medical services provided for the patients 44. The flow of money may continue smoothly until the TPP's 48 payments 50, 54 and 58 to stockholders 52, TPP management 60 and medical services providers 56, exceeds the TPP's income from patient premiums 46.

When a TPP begins to have its expenditures exceed its income, the TPP has several courses of action it may choose to take. First, the TPP may take a loan from a bank. Banks, however, generally do not loan money to TPPs to help cover their general expenditures because once a TPP falls behind in paying its outstanding expenditures, it is typically only a matter of time before the TPP will become insolvent. Second, the TPP may reduce the dividends paid to its stockholders. Stockholders, however, do not like to see the dividends from their stock decrease, and tend to sell their stock if dividends decrease in any significant way, thus, further pushing the TPP closer to becoming insolvent. While reducing stock value affects all present investors including management holding stock options, it does not directly affect the TPP's debt structure. Such reduction, however, makes further stock offerings more difficult and expensive. Third, the TPP may reduce the money paid to TPP management and employees. TPP management, however, is unlikely to vote to decrease its own compensation if there is another way to solve the problem. And fourth, the TPP may increase its present operating cash reserves by delaying or generally decreasing its expenditures. This fourth option is, from recent history, the preferred method employed by struggling TPPs.

Struggling TPPs have recently been shown to decrease their expenditures by delaying payments 54 to medical services providers, providing only partial payments for billed services, denying additional services, denying payments altogether when expenditures begin to exceed income, downcoding claims, increasing premiums, increasing co-pays, decreasing permissible drugs or allowable prescription sizes, slowing authorizations for services, limiting the number of allowable visits, shifting specialty care to primary care physicians, linking TPP enrollment with physician reimbursement, shifting financial risk to physicians, and forcing physicians to see patients after the TPP stops paying. By altering the patterns of their payments to and treatment of medical services providers, TPPs have evidently been able to temporarily extend the life of the TPP until the delayed payments catch up to them, at which point the TPP becomes insolvent. A large majority of any outstanding payments due medical services providers are lost, however, when a TPP becomes insolvent. During the time from when the TPP begins to alter its payment patterns and the time it becomes insolvent, however, a medical services provider typically does not know that the services the medical services provider is providing for patients of the TPP will not be paid.

It is contemplated, in a first embodiment of this fourth aspect of the invention, that at least a portion of the data used to calculate the relative value of medical services, such as the delay until payment is made and the percentage of the allowable billed fees paid, is tracked over time to provide an indication of when a particular TPP is coming closer to becoming insolvent. In this first embodiment, by tracking the payment history of a particular TPP in its transactions with one or more medical services providers, the point at which the TPP begins a pattern of delaying payments or paying only partial payments may be detected. By detecting such patterns, medical services providers may better evaluate the desirability of dealing with particular TPPs or accepting or treating patients from certain TPPs because of the TPPs' present inability to pay their bills on time.

In particular embodiments of this fourth aspect of the invention, an indication of worsened payment patterns by a TPP is indicated to medical services providers to assist in such decisions as entering into an agreement with a TPP, accepting a new patient of a TPP, scheduling a patient's appointment, and visiting with a patient. In other particular embodiments of this fourth aspect of the invention, a worsened payment pattern is automatically considered as a factor in ranking a TPP or patient, or determining the best duration for a visit with a patient. It is also contemplated that an improved payment pattern may be useful in some situations for evaluating the desirability of entering into an agreement with a TPP, accepting a new patient of a TPP, scheduling a patient's appointment, or visiting with a patient. It is anticipated that by providing medical services providers with an indication of worsened payment patterns by TPPs as a substantially real-time indicator of the financial viability of the TPPs, the payment patterns of TPPs generally will improve. It is also anticipated that an early warning system will place the TPP on notice that its behavior is being monitored in real-time and that unethical accounting practices will be observed. This should hasten the devise of financially inadequate TPPs.

According to a fifth aspect of the present invention, a database is provided for storing, collecting and updating relevant data for calculating the relative value of services as described in relation to the various embodiments of the present invention. The database preferably includes data for one or more, and preferably all, TPPs such as, by example only: the allowable fee schedules; a payment history for each services type; an insolvency indicator; TPP patient demographics, and the like. A separate or an associated database or fixed selection may also include data relating to: the operating costs of one or more specific medical services providers; collection costs; a desired profit threshold; rank indicator parameters; investment interest amounts; inflation amounts; and the like.

In a first embodiment of the fifth aspect of the invention, a database such as that described herein is provided in a stand-alone computer memory such as a hard drive of a conventional laptop or desktop computer. In a second embodiment of the fifth aspect of the invention, the database is stored in a computer network server or mainframe computer, and accessible from any one of a plurality of local and/or remote computer terminals such as is described later herein. The local and/or remote computer terminals may access the network server through any communication means known in the art including, but not limited to, direct wiring, telephone wiring, radio wave, cellular or other wireless technology, the Internet, or any other method of accessing a computer network server known in the art. In a third embodiment of the fifth aspect of the invention, the database, stored on a computer network server, updates its contents through communication with a plurality of sources including one or more other medical services providers. In this third embodiment, it is contemplated that the data for the TPP payment histories and other TPP-related information may be retrieved from a plurality of medical services providers each subscribing to a service allowing access to the database. By compiling data from numerous sources, a more accurate estimate of the relative value of a particular service, and other data used in generating rankings, etc., may be obtained.

According to a sixth aspect of the present invention, during a primary medical personnel contact with a patient, a primary medical personnel may provide the patient with a broader range of information relevant to the visit. By example only, using a specific situation, suppose a medical physician examined and diagnosed a patient with a cancerous tumor and indicated that the only two options were either chemotherapy or radiation therapy to reduce the size of the tumor, and surgery to remove the remainder of the reduced tumor. According to this sixth aspect of the present invention, the physician is not limited to the pamphlets on hand or the physician's memory for explaining the alternate procedures and risks involved. In a first embodiment of the sixth aspect of the invention, the physician has immediate access to a database of medical information from which the physician may print the required information to show to or give to the patient. In a second embodiment of the sixth aspect of the invention, the physician may retrieve pre-formed lists of recommended reading material from a database and print it for the patient. In a third embodiment of the sixth aspect of the invention, rather than printing information for the patient, the physician may automatically send the information to the patient by facsimile or email.

According to a fourth aspect of the present invention, the physician may request books, pamphlets or other reading material for a patient such as by: indicating one or more selections for an assistant to retrieve and deliver to the patient when the visit is done; ordering the materials for the patient using an on-line Internet book sales company such as www-.barnesandnoble.com for automatic delivery to the patient; or indicating a patient preference for particular materials and having the materials delivered to the patient. In an embodiment where the physician indicates selections for an assistant to deliver to a patient when the visit is done, a physician is preferably provided with wireless or other access to a networked computer system to provide the selection indications to the assistant such as a receptionist. The physician's access may be any device configured to provide electronic signals to the computer system such as a handheld computer, a pen tablet, laptop, desktop or other computer including software for accepting the indications. While discussing the required procedures and risks with the patient, the physician may indicate the desired materials and automatically send the indication to the assistant to retrieve. In an embodiment where the physician orders on-line, the physician's access includes software for sending an order to an Internet sales company or other company by email or facsimile. The physician may enter a patient's credit card or other account number, or may have an outstanding account with the sales company and bill the patient through the physician's own billing system. After ordering, the materials may be delivered automatically to the patient by any method provided by the sales company. For any embodiment of this sixth aspect of the invention, however, the physician may request the physician's recommended materials only, or may provide the patient with a selection of materials from which the patient may choose materials for the physician to request.

In a fifth embodiment of the sixth aspect of the invention, to assist the physician in better explaining the information to a patient, the physician is provided with access, preferably wireless, to a database of presentation and other media materials on a variety of subjects. Preferably, the physician's office includes a computer monitor at which the physician may interact with the database to display multi-media presentation materials such as video clips, graphical presentations, and the like. The computer monitor may preferably be configured as a pen tablet, as described herein, from which the physician may quickly and easily show the presentations from anywhere in the physician's office.

According to a seventh aspect of the present invention, the physician sends a prescription to a pharmacy by email, facsimile, or by accessing the pharmacy's Internet site (such as www.drugstore.com), and orders the prescription for delivery directly to the patient's home. Medical statistics indicate that approximately 25% of all prescribed medicines are not picked up by patients. Even under present medical management systems where prescriptions or refills may be sent to pharmacies, there is a percentage of people who will forget to pick up the filled prescription or who will choose not to pick it up. By having the prescription automatically delivered to the patient's home or work address, the patient will be more likely to use the prescription and to realize a benefit of the medical services. In conjunction with previous aspects of the present invention, the prescription may be paid for by a patient's credit card or other account information sent with the prescription, billed by the pharmacy filling the prescription, paid by the medical services provider or otherwise included with the medical services provider's account and billed through the patient's TPP, or paid by the medical services provider and reimbursed by the patient immediately upon delivery. For embodiments where the medical services provider provides payment for the prescription and bills the patient's TPP, the relative value of ordering the prescription for the patient is certainly relevant and a service charge may be added to cover the added expense incurred by the medical services provider. Additionally, if a patient's TPP has a bad rating, it is contemplated that prescription billing and delivery services may not be offered to some patients.

In a conventional medical services provider's office, when a primary medical provider, such as a physician, completes a visit with a patient, the primary medical provider also generates a "superbill" and delivers it to an employee of the medical services provider such as an accounting or data entry clerk. The "superbill" is conventionally a paper record which includes a list of services provided to the patient for billing to the TPP after the information has been appropriately entered into a standard TPP claim. According to an eighth aspect of the present invention, a primary medical personnel records the "superbill" information into an electronic form on a pen tablet or other handheld electronic device which may be directly downloaded to a billing database and sent to a TPP immediately. By recording the "superbill" information in a form which may be directly downloaded and immediately billed to the TPP, errors from misreading a physician's handwriting or miscopying the information may more easily be avoided, and payment may be received more quickly from the TPP.

According to a ninth aspect of the present invention, a fraud security system based on biometric is employed in a medical services provider office. According to a first embodiment of the ninth aspect of the invention, a computer is equipped with a biometric identifying device such that when an employee uses the computer, or in some embodiments when the employee approaches the computer, the employee's biometrics are detected and identified as unique to that employee. Specifically, a biometric identifying device may include a finger print or facial print identifying device, a retinal scanning device or any other device which can uniquely identify the employee. Once the employee is identified, the employee is "clocked-in" for work and/or "logged-in" to a particular computer. The employee's entries into a particular computer may be uniquely identified as belonging to the employee and to no one else. Routine checks of the identity of a computer user may also be employed, such as by a routine retinal or facial scan from a portion of a computer monitor, or by a routine finger print scan from a key on the keyboard if desired to further tighten security. This will also simplify signing onto a system and remove the need for office staff to remember a series of passwords for various systems. Each employee, based upon their unique identifier, may be assigned a level of security clearance and automatically be granted access to appropriate information by an associated microprocessor. Additionally, automatic daily balance sheets may be generated to ensure that the amount of money in the money drawer matches the amount which should be there based on the patients seen, and that the dates of co-pay amounts paid have been accurately recorded.

Supplies for medical services providers' offices are conventionally ordered in bulk when the number remaining of a particular supply is low. The result of this method of ordering is that certain supplies which are used infrequently sit unused for long periods of time, some of which have expiration dates which may expire before they are used. This method of ordering, similarly, is inadequate if in a particular month there are enough of a particular supply that additional supplies were not ordered, but there are too few of the supply to meet that month's need. When a particular supply runs out, delivery time is required for new supplies and for that time, the needed supply is inconveniently unavailable. According to an tenth aspect of the present invention, supply use patterns are monitored and evaluated in conjunction with scheduled patient treatments and actual inventory to assist in ordering only those supplies which will be needed within a predetermined period. The embodiments of the present invention also enable more reliable control of certain high cost supplies (such as anti-cancer agent pharmaceuticals).

For example, a database including lists of supplies by identification number may be updated for each order period (typically weekly or monthly) with existing office inventory. Software having access to the database may also calculate an average use of a particular supply during each order period and identify the supplies which will likely be used for scheduled medical services during the upcoming order period. If there are thirty throat culture kits remaining in inventory and the physician's office uses an average of fifty kits in a month, the physician's office may order between twenty and thirty additional throat culture kits to cover the next order period's predicted use rather than waiting until the physician's office is on their last box and trying to rush an order of three-hundred kits. However, if, at the beginning or even at some point in the middle of an ordering period, the physician's office already has more appointments scheduled relating to sore throats than is average for that time, appropriate adjustments may be made to the number being ordered for that period, or additional supplies may be ordered between ordering periods to compensate for the anticipated shortage. According to an embodiment of the present invention, a medical services provider may associate with a particular medical supply retailer and automatically order medical supplies over the Internet through software associated with the order-anticipating software, the software ordering the anticipated amount without the need for staff intervention. Supply and inventory management may also be accomplished by lowest cost bidding auctions for participants if desired.

As will be clear to one of ordinary skill in the art, any number of the previously described aspects of the present invention may be incorporated into a system for use by a medical services provider. The following medical management system, as shown and described in FIGS. 4 and 5, is only one example of how the various aspects of the present invention may be implemented in combination.

Figure 4:
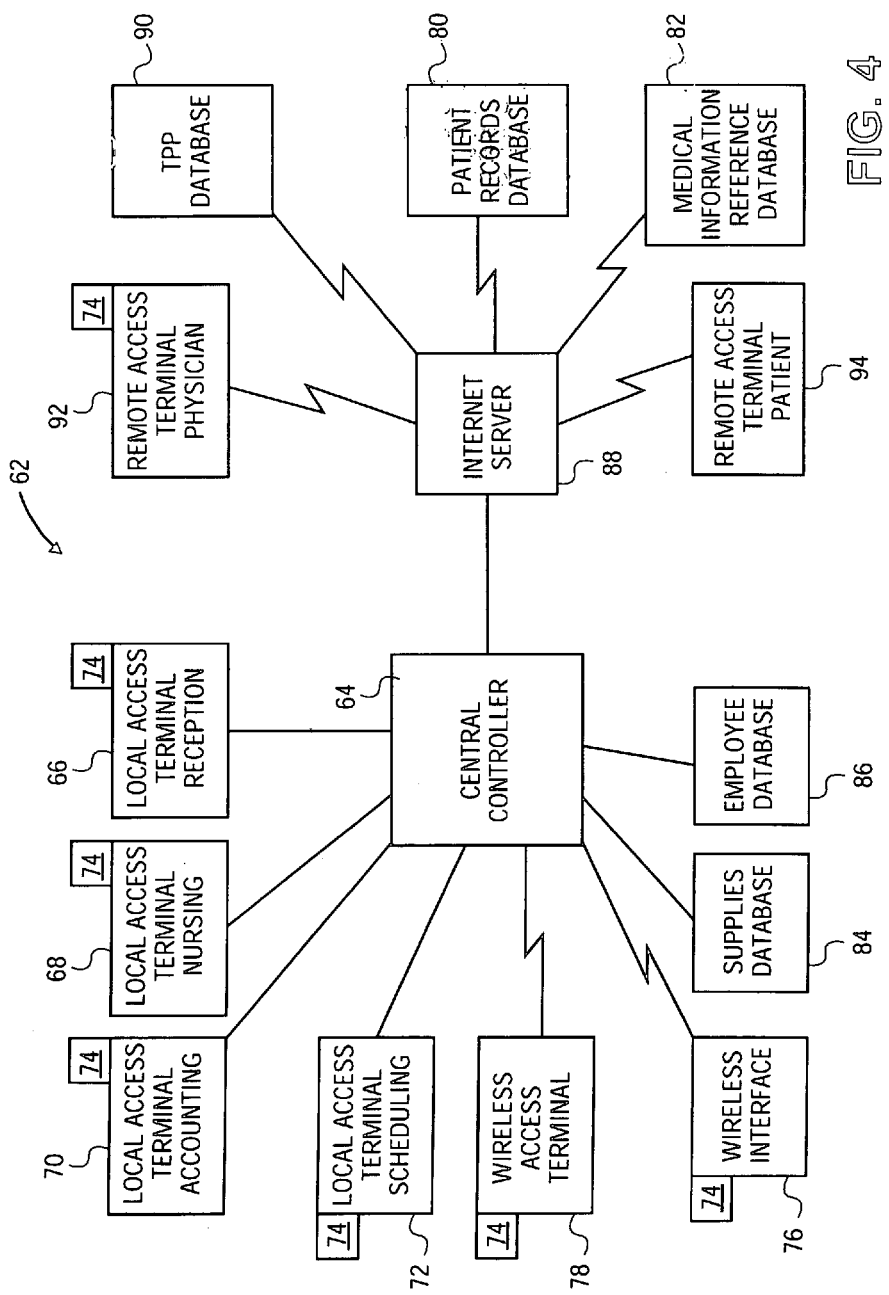
FIG. 4 includes a general system diagram illustrating a medical management system according to an embodiment of the present invention.
Figure 5:
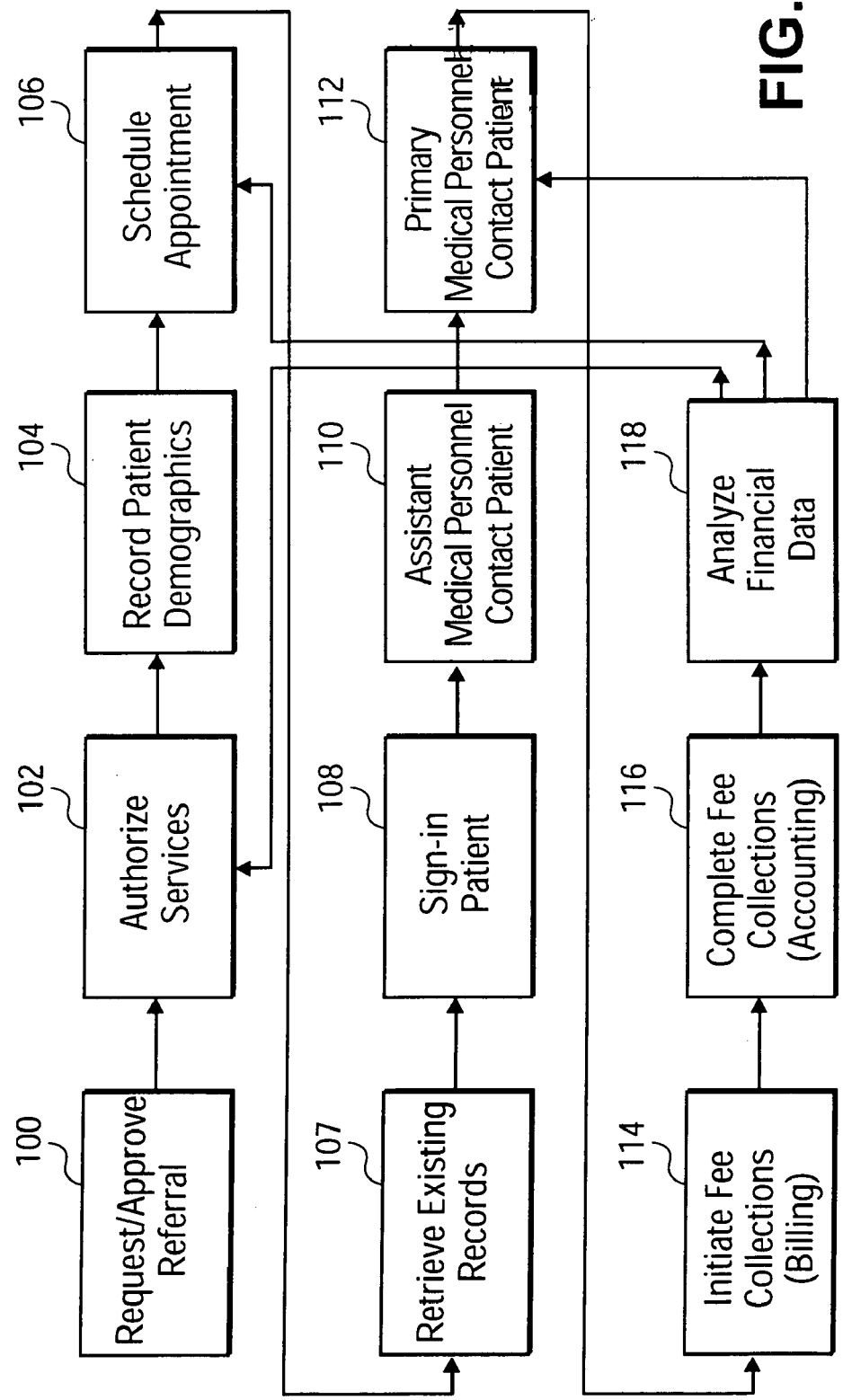
FIG. 5 includes a flow diagram illustrating a medical management process for each contacted patient according to an embodiment of the present invention.

FIG. 4 shows a block diagram of an embodiment of a medical management system 62 in accordance with various aspects of the present invention. The medical management system includes a central controller 64 for enabling interconnection between the various associated parts of the system 62. The central controller 64 may be configured as a local computer network server such as those distributed by Micron, Inc. of Boise Id., or any other computer network server well known to those of ordinary skill in the art. The operating system supported by the controller will vary depending on the basic operating system selected by a particular medical services provider, but is preferably a Windows 95/NT based system. Associated with the central controller 64 are a plurality of local access terminals 66, 68, 70 and 72 through which access to the medical management system 62 may be attained. It is contemplated that the hardware for each access terminal is preferably a conventional desktop computer or other electronic device such as that distributed by Gateway Computers, IBM or Macintosh. Electronic devices, such as desktop computers, their capabilities and operation are well known to those of ordinary skill in the art and it is believed that one of ordinary skill in the art may readily select appropriate access terminals, and network servers given the software requirements for the system. Presently, the preferred electronic device for the present system is a Windows 95/NTbased system having a 300 MHZ Pentium speed processor or better and a hard drive large enough to store the necessary software and local data for the purpose of each terminal or server. As will be clear to one of ordinary skill in the art, each appropriate access terminal may inherently also include one or more of an associated display device, input device, modem, direct or wireless network connection, printer, or other peripheral device as required to enable the purpose of the access terminal or database. Such peripheral devices are well known to those of ordinary skill in the art.

Each local access terminal 66, 68, 70 and 72 most preferably has associated therewith a biometric identification device 74 such as a finger print, face print or retinal scanner. Software for performing the functions required by each local access terminal 66, 68, 70 and 72 is included on the respective access terminals hard drives. For example, on a local access terminal 72 from which it is desirable to schedule appointments scheduling software configured according to embodiments of the present invention is included, and on a local access terminal 70 from which it is desirable to perform accounting tasks, accounting software configured according to embodiments of the present invention is included.

Also associated with the central controller 64 is one or more wireless interfaces 76 or wireless access terminals 78. In simple embodiments, the wireless interface 76 may include a handheld computer such as a Palm Pilot or other microprocessor with a small screen. Additionally, the wireless interface includes a microphone and voice recognition capabilities to reduce the need for transcription. Voice recognition software such as Dragon, distributed in association with Microsoft Office products, are well known to those of ordinary skill in the art. The wireless interface 76 includes software to enable a physician or other medical personnel to complete forms, update simple documents, record and submit "superbills", and the like. A computer programmer of ordinary skill in the art will readily be capable of programming the required software given the requirements of a particular system. In more complete embodiments, a wireless access terminal 78 is used by which complete access to the central controller 64 connections may be obtained. The wireless access terminal 78 is preferably configured as a pen tablet such as the Stylistic 2300 distributed by Fujitsu, Inc. of Japan.

Through a Windows-based software interface on the wireless access terminal 78, it is contemplated that a physician or other authorized medical personnel may: directly access and view patient medical records in a patient records database 80; access a medical information reference database 82; provide presentations to patients through presentation software; generate "superbills"; dictate reports and letters through voice recognition software; automatically send letters and reports to referring physicians by facsimile or email; access and review test results; prescribe medicines and have those medicines delivered directly to patients. Also associated with the central controller 64 is a supplies database 84, containing historical use data regarding specific supplies, inventory data, ordering information, and the like, and an employee database 86 containing employee information such as the information required to automatically grant employees appropriate access to authorized portions of central controller 64 data and associated interfacing software without the employee being required to enter a different password for each database or software sub-system.

The central controller 64 may also have access to the Internet through an Internet server 88 in communication with the central controller 64 through a communications device such as a wireless communication device, modem, computer cable or other electronic signal conductor. In the present embodiment, the patient records database 80, the medical information reference database 82 and a TPP database 90 are available through an Internet connection so that data which may be needed at more than one location may be more easily accessed by all authorized users. Certainly, it would be in accordance with the various aspects of the present invention if the data from each of the databases 80, 82, 84, 86 and 90 were located at the medical services provider's office, or remotely located at some other location such as a database maintenance organization service which coordinates access to the databases and provides updated data and other services to its subscribers.

To enable substantially real-time information on the relative value of services provided to a patient of a TPP, and to quickly retrieve patient records, it is preferable only that the data be available for access by an authorized user through appropriately configured software. By having the TPP database 90 and the patient records database 80 available by numerous users at various locations, the information therein may be regularly updated by using data from several locations, making the databases more useful. By having the medical information reference database 82 at a central location and accessible through the Internet, it is not necessary to store the information reference database 82, which is likely to be rather large, at every location. However, for information which may be specific to a particular location, such as which pamphlets are available in stock, it may be preferable to also include a portion of the information reference database 82 at the medical services provider's office location.

Through a remote access terminal 92 such as a home computer with an Internet connection, a physician may gain access to the central controller 64 for working from home or some other remote location. In some applications, it will be desirable to also include a biometric identifying device 74 at the remote access terminal 92, although this is certainly not practical or desirable in all situations and conventional password security will likely be required. Patients, too, may access the central controller 64 through a remote access terminal 94 to enable the patient to review the patient's appointment schedule, read medical references, schedule new appointments, and the like. It is anticipated that patients may establish an access account through a medical services provider to gain access to certain data available through the medical services provider's central controller 64.

FIG. 5 is a basic process chart indicating general categories of sub-processes which may occur for each patient contact under embodiments of the present invention. The following example in reference to FIG. 5 is one embodiment of a method referencing many aspects of the process a medical services provider goes through to provide medical services to a patient. The process described hereafter involves a medical services provider subscribing to a data tracking service which tracks the payment patterns of TPPs through its subscribers or by other means, and provides the information to medical services providers through licensed software packages. The data tracking service also provides electronic medical files for rapid transfer between offices subscribing to the same service.

More than 98% of referral requests 100 are granted by TPPs. This high rate of approval by TPPs makes the referral request process nearly obsolete in modern TPP practice. Therefore, under an embodiment of the present invention, if a referral 100 is required prior to a medical services provider visiting with a patient, the referring medical services provider contacts the patient's TPP through the Internet, inputs the appropriate visit type (and associated code number), the patient's name and TPP reference number, and the patient is automatically granted approval, or rejected based on the TPP coverage of the patient's associated TPP plan.

Figure 6:
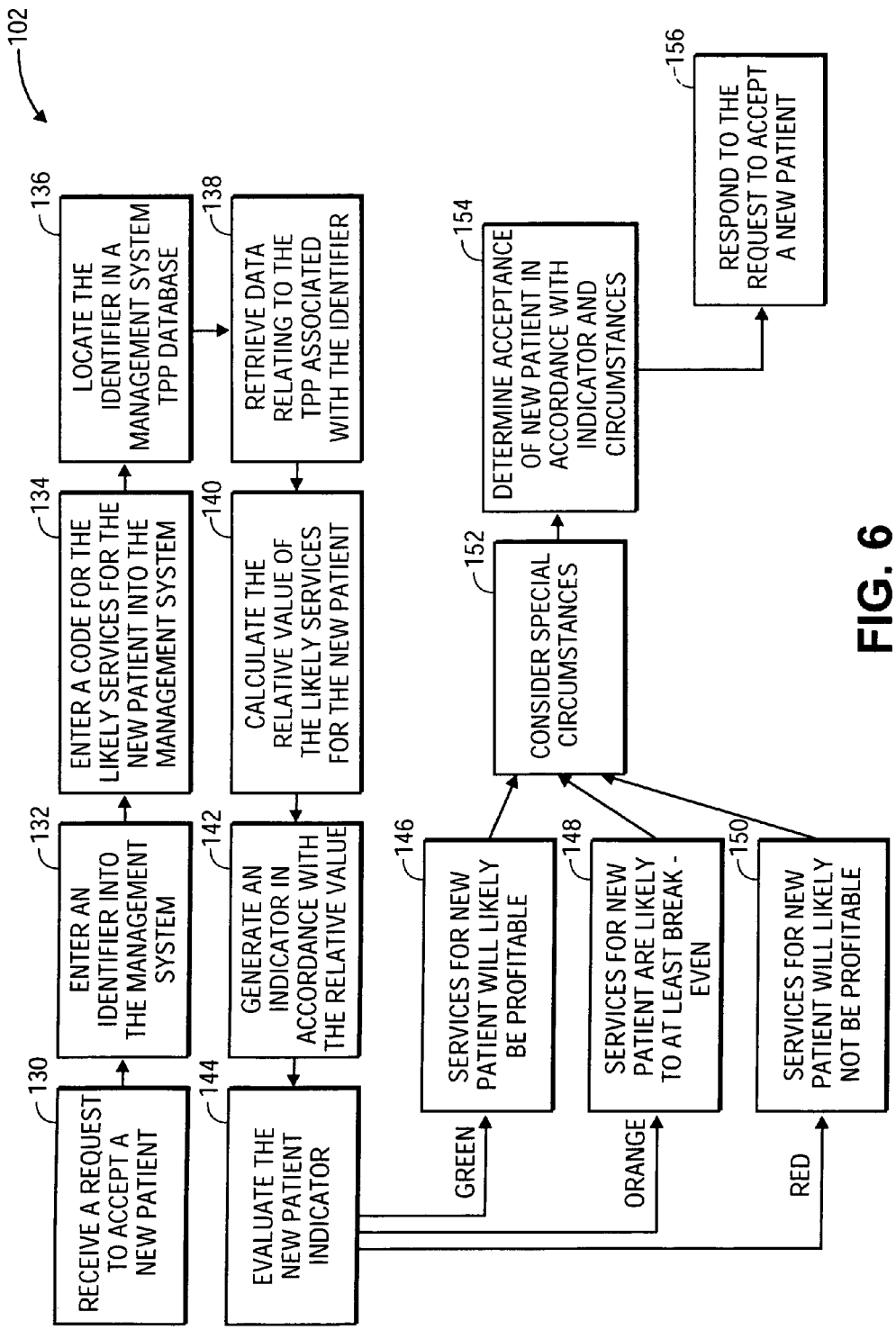
FIG. 6 includes a flow diagram illustrating a process for determining whether to accept a new patient.

After the TPP has granted the referral request, the medical services provider to which the referral was made, or any medical services provider accepting a new patient, must decide whether to accept the new patient and authorize 102 its own medical staff to treat the patient. As shown in the flow diagram of FIG. 6, under an embodiment of the present invention, as part of the authorization process 102, a medical services provider staff member, such as a receptionist, new patient secretary or scheduling clerk, receives a request to accept a new patient 130 and collects at least a TPP identifier, but preferably more detailed introductory information relevant to the new patient such as the patient's TPP, TPP plan, name, address, gender, age, and the like, and enters the data into a computer terminal in communication with a patient database and evaluation software. The staff member enters the identifying information into the management system 132, and a code for the type of services the patient will likely be receiving 134. For example, if the medical services provider is a gynecology clinic and the new patient is pregnant, a relevant code may be entered. Alternatively, if the medical services provider is a general family practice clinic, and the new patient is a child, a different relevant code may be entered corresponding to the likely services which will be provided to a child as opposed to an adult. Software operating on the staff member's access terminal locates the identifying information in a management system database 136 and associates an appropriate TPP with the identifier to access and retrieve the TPP's data 138. The management system, having evaluation software and using information in a TPP database such as the TPP's previous payment patterns to this and other medical services providers, the estimated relative value of the likely services to be provided to this patient 140, and the like, generates an indicator of the relative value of the services in accordance with the calculated relative value 142, and provides the medical services provider staff member with an indication (e.g. red, orange, or green indicator symbols) of whether it would be profitable for this medical services provider to accept this new patient. In the example shown in FIG. 6, if a green indicator is generated, this corresponds to an indication that the services for the new patient will likely be profitable for the medical services provider 146. Contrarily, if a red indicator is generated, this corresponds to an indication that, based on the payment patterns of the TPP, its financial strength, or other reasons, services provided for this new patient will likely not be profitable for the medical services provider 150. If an orange indicator is generated, this may correspond to an indication that services for the patient are at least likely to break-even for the medical services provider 148. The staff member evaluates the new patient indicator 144 and any other special circumstances 152 which may exist. Special circumstances may include such circumstances as the urgency of the new patient, the identity of the new patient, any additional conditions which may be placed upon this new patient to better ensure profitability for services provided, and the like. The staff member may then determine whether to accept or deny the new patient 154 and respond to the request 156. If the patient has been seen by other medical services providers also subscribing to the same data tracking service, the patient's information will already be recorded in the system and the data may be confirmed and updated, if needed, and used to obtain an indication of authorization.

Figure 7:
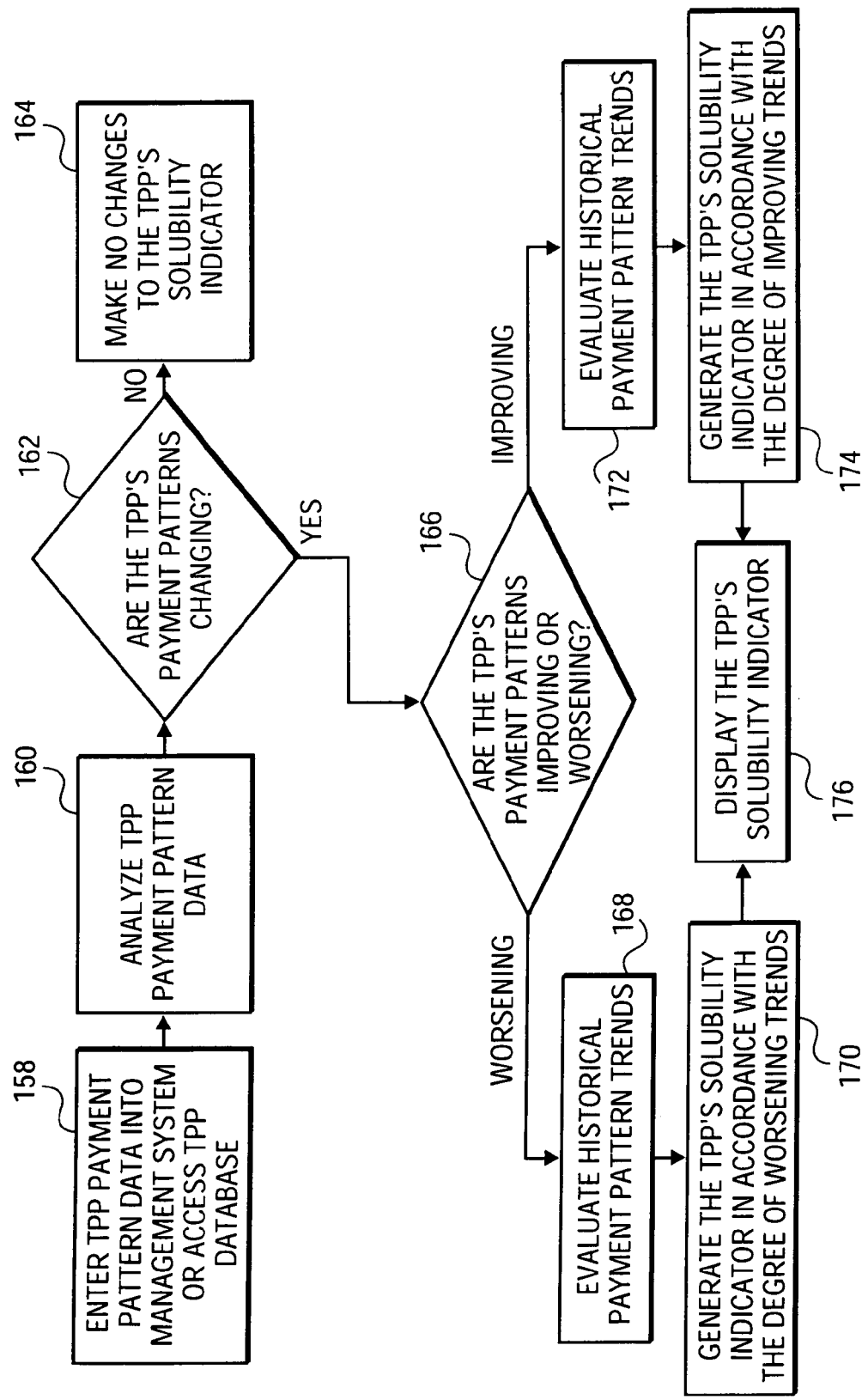
FIG. 7 includes a flow diagram illustrating a process for generating a solubility indicator.

The evaluation software may also provide an indication of the estimated financial strength or solubility of the TPP based on recent trends in the TPP's payment patterns. As illustrated by the flow diagram of FIG. 7, to evaluate the solubility of a TPP, a medical services provider staff member enters data relating to a TPP's payment patterns into a management system access terminal or otherwise accesses the management system's TPP database 158. The management system, or one of its associated access terminals operating with appropriate software, analyzes the TPP's payment pattern data 160 and determines whether the TPP's payment patterns are changing over time 162. If the TPP's payment patterns are not changing, the software generates a solubility indicator for the TPP based upon its payment patterns or otherwise indicates 164 that there is no apparent indication of a threat of insolubility. If there are changes in the TPP's payment patterns, the software evaluates whether those changes are improving the payment patterns of the TPP, or whether the payment patterns are getting worse 166. If the payment patterns are worsening, the software evaluates the historical payment pattern trends 168, such as extreme recent changes in payment patterns, moderate changes in payment patterns over a long period of time, or regular periodic improving and worsening of payment patterns. The software then generates a solubility indicator for the TPP in accordance with the degree of worsening payment pattern trends to represent the threat of the TPP becoming insolvent. Low solubility rankings may indicate a likelihood of the TPP becoming insolvent soon, or that the TPP has difficulty paying its bills on time or in full, and high solubility rankings may indicate a relatively smaller likelihood that the TPP will ever become insolvent, or that the TPP pays its bills on time and in full. The purpose behind using the historical payment patterns of a TPP to determine the likelihood of the TPP becoming insolvent is the trend of TPPs to begin adjusting their payment patterns to postpone their immediate expenditures in an attempt to remain solvent. Similarly, if the TPP's payment patterns are improving, the software evaluates the historical payment pattern trends 172, and generates a solubility indicator for the TPP in accordance with the degree of the improving trends 174. Once a solubility indicator has been generated, it is displayed to the staff member 176.

Once the patient has been accepted as a patient, assuming the patient's information is not already in the system by downloading it from the data tracking service, a medical services provider staff member enters the patient's demographic information 104 into the computer terminal for association with the patient database. Alternatively, the patient may be provided with a wireless access terminal such as a Fujitsu, Stylistic 2300 pen tablet configured with software to display an electronic form which the patient may fill-out to include the patient's medical history, guarantor, and other necessary demographic information. The computer terminal or wireless access terminal of the present invention is in communication with the TPP and patient databases through an Internet connection so that all of the information in those databases may be available to authorized users at many locations. The patient is also asked whether the patient would like to establish an online prescription ordering and reading material ordering account either through the medical services provider or through one of several online services, and whether the patient would like to establish an account to check the patient's medical records and appointment schedules through the Internet or by email.

After a patient is accepted as a new patient and has the required demographic information stored in the patient database, at some point the patient will likely desire to schedule an appointment 106. As illustrated by the flow diagram in FIG. 8, when a patient calls in to schedule an appointment 178, a medical services provider staff member with access to an appropriately configured computer terminal will receive the call and enter a patient identifier 180 such as the patient's name and/or TPP plan number into the terminal to access the patient's information. The staff member may then also enter a predetermined code for the type of appointment or medical services the patient is requesting 182, and with which physician the patient would like to visit. Appropriately configured software operating on the access terminal searches a management system patient database to locate the patient identifier which was entered 184, and correspondingly retrieves a TPP identifier and associated data relating to the patient's TPP 186. Using the TPP's payment pattern data and other relevant data, the software calculates the relative value of the requested appointment 188 to the medical services provider, and generates an appropriate scheduling indicator 190 in accordance with that calculated relative value. The scheduling indicator is displayed on an access terminal display for the staff member to evaluate 192 prior to responding to the request to schedule the appointment 204.

Figure 8:
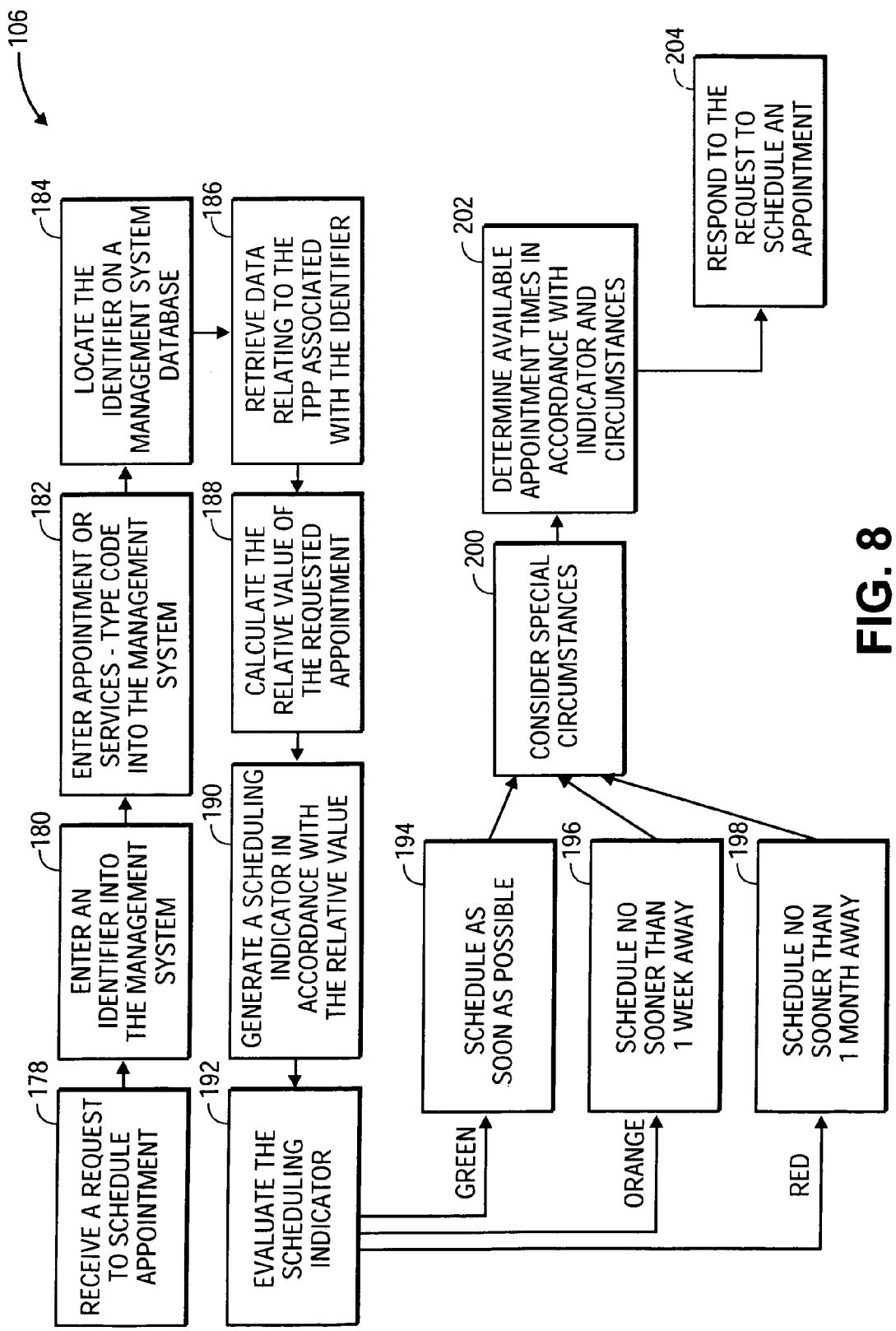
FIG. 8 includes a flow diagram illustrating a process for determining when to schedule an appointment.

According to the embodiment shown in FIG. 8, a green scheduling indicator represents an indication that the requested appointment will likely be very profitable for the medical services provider and that an appointment should be scheduled as soon as possible 194. An orange scheduling indicator represents an indication that the requested appointment should be scheduled no sooner than one week away 196, and a red indicator represents an indication that the appointment should be scheduled no sooner than one month away 198. By scheduling appointments for the most profitable medical services first, or those with the highest relative value to the medical services provider, medical services providers may more effectively maximize their profits. In addition to the scheduling indicators, there may be other special circumstances 200 which should be considered by a staff member in scheduling an appointment. Such special circumstances may include the urgency of the treatment needed, the identity of the patient, other conditions which may be placed upon the patient to increase the likelihood of profitability for the medical services provider, and the like. The staff member then determines available appointment times in accordance with the scheduling indicator and special circumstances 202, and responds to the request to schedule and appointment 204.

In establishing acceptable parameters for appointment scheduling, resource scheduling, relative value calculations and the like, it is contemplated that a medical services provider may select from a menu of options to define at least a portion of the boundaries and data for the various indicators. Such boundaries and data may include data related to, but not limited to, a break-even point, or, more specifically, the operating costs for each individual procedure, the costs for various supplies needed for each procedure, the overhead costs for the facility, lost investment returns rates, collection costs at various points in collection, and the like.

Additionally, as part of scheduling, the medical services provider staff member may adjust the length of the visit within recommended or selectable limits for a particular visit type so that the visit request may raise a green indicator rather than an orange indicator, or an orange indicator rather than a red indicator. By adjusting the length of the visit to make the length of the visit more closely match the expected relative value of the TPP payment, patients who would otherwise have been unprofitable, may be seen. When the appointment is scheduled, the required assistant medical personnel, supplies, rooms, etc. are each automatically scheduled and may optionally be scheduled based, in part, upon the appointment value indicator. Preferably, the scheduling software automatically checks for the availability of the staff, supplies, rooms, etc. while checking for the availability of the primary medical provider.

Sometime before the patient arrives for the patient's appointment, a medical services provider staff member checks for a patient's medical records 107 on the patient database, and if the records are not there, orders them from a referring medical services provider or other previous medical services provider, or generates new patient medical record forms for the patient. If the records were not presently in the patient database but are available, the records may be entered into the database, scanned into the database, or otherwise included in the patient database for future use by authorized personnel.

When the patient arrives for a visit, a medical services provider staff member greets and "signs-in" the patient 108 and indicates on a computer terminal that the patient has arrived. When the room for which the patient is scheduled becomes available, an assistant medical personnel, having access to a computer terminal indicating that the patient has arrived, contacts the patient 110 and collects preliminary information such as the patient's weight, temperature, blood pressure and pulse rate. The assistant medical personnel carries a wireless access terminal such as a Fujitsu, Stylistic 2300 pen tablet configured with appropriate software to access the patient records database and records the patient's preliminary information in an appropriate electronic form associated with the patient's medical records for the present visit. The assistant medical personnel also records on the electronic form such information as the specific reason for the visit, confirms any medication the patient is presently taking, and may confirm other information associated with the patient to ensure accuracy if time permits before the primary medical personnel arrives.

When the primary medical personnel arrives to contact the patient 112, the primary medical personnel takes the assistant medical personnel's wireless access terminal having the patient's medical records thereon, or otherwise transfers the data and partial electronic form to the primary medical personnel's wireless access terminal. A timer indicating the total time recommended for the visit with the patient and the recommended time remaining for the visit is provided on the wireless access terminal to provide the primary medical personnel with an indication of how long the visit should last to at least break-even on the appointment. The primary medical personnel, preferably within the recommended time, checks the patient's present complaints, reviews the patient's physical systems, diagnoses any problems, and makes recommendations for treatment. While the primary medical personnel is evaluating and managing the patient's complaints, the primary medical personnel may dictate the necessary reports to the patient's medical records through the wireless access terminal which is configured with voice recognition software. The primary medical personnel may also dictate a letter or otherwise send a report to a referring medical services provider and send that report by email, facsimile, or have it printed on a network printer by access through the wireless access terminal. In indicating recommended treatment on the patient's visit record, appropriate related forms will also automatically be generated in response to the primary medical personnel's indications. For example, if the primary medical personnel recommends surgery, a form will automatically be generated and appear to enable the primary medical personnel to schedule the surgery, including obtaining TPP approval, obtaining informed consent from the patient and instituting the required orders and charges. If, however, the primary medical personnel indicates a prescription is recommended, a list will appear of recommended medications for the indicated problem, TPP approval may automatically be obtained through the Internet if prescription approval is available or required, an electronic prescription will be generated, potential drug interaction problems will be indicated, and all other information relevant to one or more selected medications, such as side effects, instructions for use, interactions, etc. will be available to the primary medical personnel and printable on the screen or on a network printer. If the patient has established an account to automatically order the prescription, the primary medical personnel need only indicate that the prescription should be sent, and the prescription will be filled by the patient's previously indicated, preferred method of receiving the prescription such as next day delivery to the patient's home.

In explaining any required procedures, medication, conditions, etc., to the patient, the primary medical personnel may select from a database of reading material, presentations, illustrations, research, investigational studies, and the like, which may be immediately displayed to the patient to assist the primary medical personnel in the explanation, or which may be printed from a network printer for the patient, or emailed directly to the patient through a pre-established account. Additionally, if the patient desires additional information, the primary medical personnel may display a list of recommended reading on the desired subject including relevant prices and, if requested by the patient, order one or more recommended reading selections through an online bookstore for automatic delivery to the patient's home.

If, in diagnosing a condition, the primary medical personnel has, previously, ordered laboratory tests be performed, the laboratory tests may be accessed directly from the laboratory performing the tests through the Internet connection on the wireless access terminal, or may be accessed within the patient's medical records. If a series of laboratory tests has been performed, not only may the primary medical personnel access each laboratory test individually, but he or she may view an historical trend of laboratory results which includes graphs of changes in the laboratory results over time. The laboratory tests results viewer software also provides indications of abnormal test results or trends. Laboratory tests, if indicated as a recommended treatment, may also be automatically ordered through an appropriate electronic form generated in response to the indication of a recommended laboratory test.

After the patient's appointment is over, the patient returns to a medical services provider staff member and, if the patient has not already paid a required copay amount, pays the copay amount, schedules further appointments as necessary, receives any reading material indicated by the primary medical personnel, receives a printed prescription if required and not automatically ordered, receives any other receipts or referral letters or records as necessary, and leaves. The copay may alternatively be required prior to service.

If the patient's TPP plan requires a copay, a computer terminal accessible by the medical services provider staff member indicates clearly to the staff member that a copay amount is required, and requires either an indication from the staff member that the copay amount has been paid (in which case the copay amount will be in the money drawer) or why the copay amount was not paid and when it will be paid. As with each access terminal in the medical management system, a security system controls access to the central controller and any data stored on any access terminal or database, and generates a record of who was using the access terminal at what times. The security system access may be granted through a password to identify each user or more preferably by biometric identifying devices such as a fingerprint, face print or retinal scanning device. An employee database associated with the central controller stores data to indicate the level of information clearance permitted by each user and data indicative of each employee's associated passwords and/or biometric data. At the end of each user's time at the computer, or at the end of each day, a daily balance sheet and report of the quantity of money which should be in the drawer is printed and the drawer is counted and the amount confirmed. Alternatively, a report may be printed by which a succeeding user or an administrator may check the drawer balance before continuing use.

The other access terminals such as the assistant medical service personnel patient monitor terminal, the scheduling terminal, the new patient acceptance terminal, the patient demographics remote access terminals, the medical records terminals and the remote access terminals used by the assistant and primary medical service personnel to track a patient's visit, each include either a password acceptor or a biometric identifying device to grant access to the software, data and systems permitted by a particular user. Each system may, in some embodiments, be configured identically with the same software and hardware (with the exception of the wireless systems which would include different hardware with the same capabilities) so as to be interchangeable. Other embodiments would include specialized software on each system to enable the system only to access the data and systems required for using the terminal in the role for which it was designed.

Figure 9:
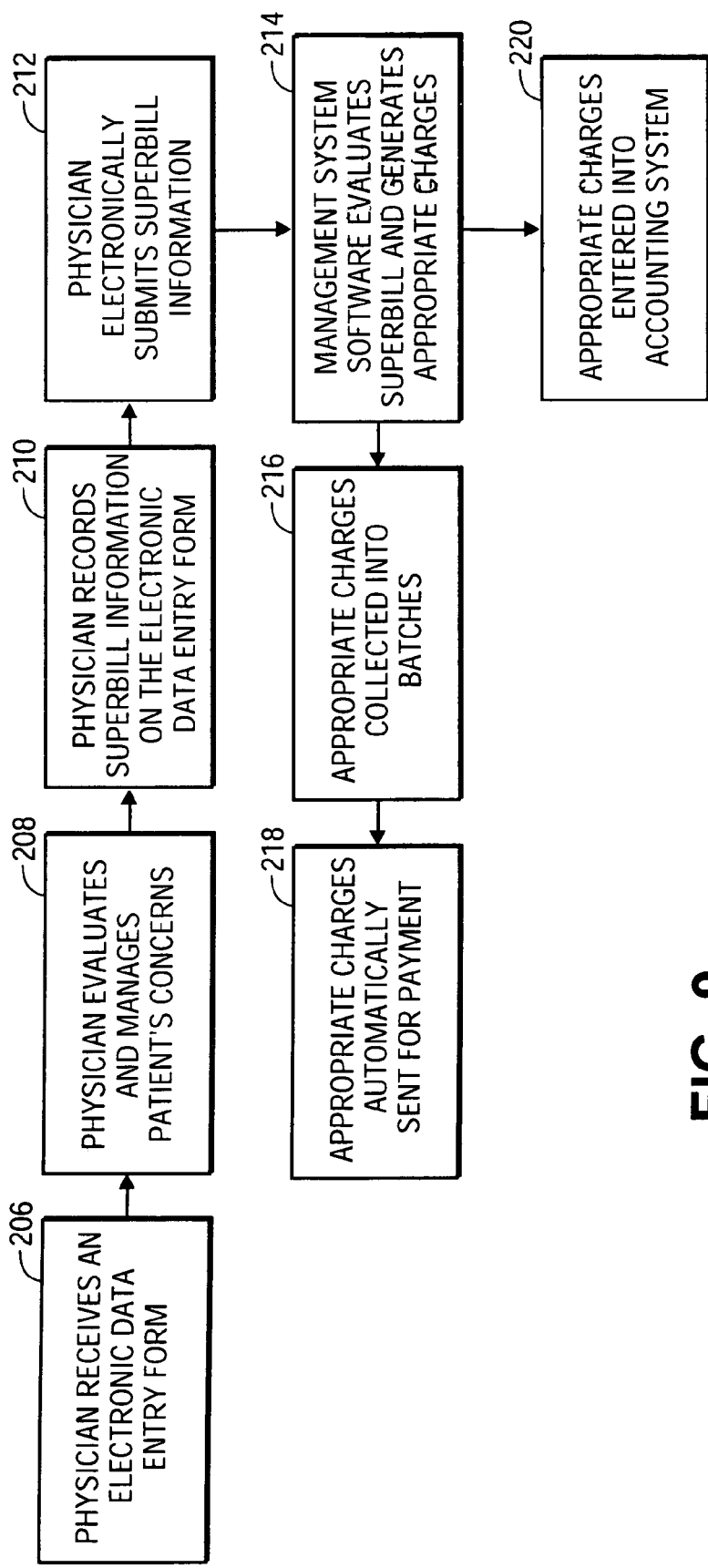
FIG. 9 includes a flow diagram illustrating a process for submitting physician superbills data for payment.

After the patient's appointment is completed, the billing process to collect the appropriate charges and fees for the visit is initiated 114. As illustrated by the flow diagram of FIG. 9, in an embodiment of the present invention, a primary medical personnel, such as a physician, is provided with an electronic data entry form 206. During a visit with a patient, the physician evaluates and manages patient concerns 208. Throughout the evaluation and management of the patient's concerns, the physician records the "superbill" information on the electronic data entry form 210 by indicating and/or selecting appropriate information as required by the form. Non-electronic "superbills" are commonly used and well known in the medical field to record patient-related charges for later billing.

When the electronic "superbill" form is complete and includes all appropriate charges, the physician, or other medical staff assistant, electronically submits the "superbill" information 212 for billing to the patient or appropriate TPP. The physician may submit the "superbill" by merely indicating that the appointment is complete, by pressing a button on the electronic data entry form, or by any other means known in the art for sending electronic data. The electronic data entry form may be displayed on a wireless access terminal 78, wireless interface 76 (FIG. 4), local or remote access terminal, or any other access terminal associated with a billing system. For the present embodiment, software operating in association with the management system evaluates the "superbill" information and generates the appropriate charges 214 for billing to the patient or TPP. Software operating within the central controller automatically enters the appropriate charges into the office management system's accounting software 220. For submitting the appropriate charges to the TPP or to a patient, the central controller either directly and immediately submits the "superbill" charges in appropriate form to the TPP over the Internet, modem, email or by other appropriate method, or bundles several "superbill" charges together in batch form 216 with other charges and data as required and automatically submit the information and charges to a TPP 218 at an appropriate time. Software which analyzes TPP reimbursement and treatment codes for medical services provided to select a code which optimizes reimbursement is well known in the art.

The present invention significantly improves payment billing time because a physician may enter the "superbill" for automatic billing without a data clerk to enter it into the system and send it out. A physician, during or immediately following an appointment, or even when performing a house call or other bed-side appointment where an accounting clerk may not be readily available, may record and submit an electronic "superbill" recorded on a portable device from anywhere access to the physician's accounting service may be obtained, including cellular transmission. By submitting the charges directly to the central controller for submission to the TPP at the next permissible interval rather than submitting a handwritten "superbill" to a data entry clerk for entry into a computer for submission to the TPP, the charges for a patient's visit more quickly reach the TPP for payment, and do not have the errors which may occur during the data entry process.

With the patient charges information appropriately recorded in the office management system's accounting software, the charges may be tracked by the system for fee collection purposes 116. The charges are compared with the allowable charges for the TPP, and the billing rules for the TPP are checked to determine if a bill should be sent directly to the patient with the patient's portion of the charges or if the TPP will directly pay the full bill. Over time, as the bill remains unpaid, accounting software associated with the management system software produces periodic reports to alert the medical services provider of the duration for which a payment has not been paid, indicate which TPP and/or patient has not paid its bill, and, in some embodiments, indicate the value lost for not yet collecting on the bill using factors such as those used to compute the NPV, administrative costs and the like.

When a patient's bill is finally paid, either by the patient or by the patient's TPP, the appropriate data is indicated to the central controller which automatically enters the data into the TPP and/or patient databases to indicate how long it took for the bill to be paid, what portion of the bill was actually paid, and the net present value of each of the individual services as if the bill had been paid at the time of the patient's visit. The database may also include any reasons provided for payment delay to track common reasons provided and analyze trends in TPP payment delays. With this information in the databases, a financial analysis 118 of the data may be performed by appropriate software programmed by one of ordinary skill in the art.

The financial analysis software, upon request by an authorized user or software system associated with the financial analysis software, generates a report detailing any TPP payment pattern generally or for specific services and determines a relative value, such as an estimated NPV, of any services requested by a patient of the TPP, an average payment delay time for the TPP, typical reasons provided for delays, and whether the payment patterns of the TPP indicate the TPP may be approaching insolvency. Particularly, as indicated in the flow chart of FIG. 5, the financial data analysis 118 may affect whether a medical services provider will authorize services 102 for patients of a particular TPP by accepting a new patient, when and for what duration the patient's appointments will be scheduled 106, and how long a primary medical personnel will visit 112 with the patient at the time of the appointment. Additionally, as indicated previously, this financial analysis will better assist medical services providers in evaluating the desirability of entering into medical services agreements with certain TPPs.

The financial analysis software also generates graphs of the profitability of the medical services provider, both generally, and in its dealings with individual TPPs as well as graphs of outstanding bill amounts for individual TPPs generally and based upon their time overdue. The general information regarding the lateness of the TPP's payments, the percentage of the allowable fees schedule amounts paid, and the reasons provided for lateness are automatically combined with the same general information from numerous other medical services providers in a common database for access by any medical services provider subscribing to the information service by appropriately configured software.

By providing medical services providers direct and substantially real-time information on the payment patterns of each individual TPP as well as software for analyzing the relative value of services requested by patients of a TPP which may incorporate any variety of costs for a medical service provider to provide the services and stay in business, medical service providers may more effectively accept and treat patients for which compensation will be received. The substantially real-time information also provides medical services providers a better indication of the potential insolvency of a TPP so that medical services providers may be aware of and control the treatment given to patients of TPPs which will be less likely to pay their bills due to upcoming insolvency.

As will be clear to one of ordinary skill in the art, the software of the various embodiments of the present invention will incorporate financial calculating, scheduling, evaluation, security, integration of a variety of systems, and other aspects of data analysis and comparison which may readily be programmed by software programmers of ordinary skill in their respective arts using known algorithms and programming modules. The hardware and much of the software components required to establish a system configured as described herein are available generally and may be programmed and configured according to the various embodiments of the present invention by those of ordinary skill in the art. As will also be clear to one of ordinary skill in the art, the data analysis and other calculations required by the present invention may be done at the site of the medical services provider by providing appropriate software on-site and accessing the required data from an information service provider, or may alternatively be done at the site of the information service provider in response to a request by the medical services provider and an appropriately configured data stream or other report distributed back to the medical services provider.

Although the present invention has been shown and described with reference to particular preferred embodiments, various additions, deletions and modifications that are obvious to a person skilled in the art to which the invention pertains, even if not shown or specifically described herein, are deemed to lie within the scope of the invention as encompassed by the following claims.

What is claimed is:

1. A medical management system comprising at least one electronic device having:
   a) a display;
   b) a memory; and
   c) a processor operating in accordance with software for:
      1) receiving an identifier associated with a third party payor ("TPP") as input;
      2) accessing data indicative of the historical payment patterns of the TPP to one or more medical service providers from which a net present value of a future payment by the TPP for at least one requested medical service for a patient associated with the TPP may be generated and assigning a rank to a patient's TPP;

3) generating an indication of the net present value of the at least one requested medical service prior to providing the medical service, the indication based at least in part upon the historical payment patterns of the TPP to the one or more medical service providers; and 4) generating an indication of when the patient is accepted as a new patient based in part on the net present value and the rank assigned to the patient's TPP;

5) generating an indication of when the patient's requested appointment should be scheduled based in part on the net present value and the rank assigned to the patient's TPP.

2. The medical management system of claim 1, wherein a payment pattern of the TPP comprises a time delay in payment of fees by the TPP, an allowable fee schedule of the TPP, and a percentage of the allowable fees paid by the TPP.

3. The medical management system of claim 1, wherein a relative value for the at least one medical service is a difference between the net present value for the at least one medical service provided and a cost of providing the at least one medical service.

4. The medical management system of claim 3, wherein the cost of providing the at least one medical service is a function of at least one of an administrative cost of a medical services provider, an overhead cost of a medical office, a cost for medical office staff salaries, an equipment and supplies cost, and a utilities cost.

5. The medical management system of claim 1, wherein the indication of the net present value is one of a plurality of ranked indicators.

6. The medical management system of claim 5, wherein the plurality of ranked indicators includes at least red, orange and green.

7. The medical management system of claim 1, wherein the identifier is an identifier of a patient associated with the TPP and the software is configured to generate an indication of whether it would be profitable to accept the patient as a new patient based at least in part upon the historical payment patterns of the TPP to one or more medical service providers.

8. The medical management system of claim 7, wherein the indication is generated as a function of the net present value of anticipated medical services to be provided for the patient.

9. The medical management system of claim 1, wherein the indication is generated as a function of the expected profitability of the TPP.

10. The medical management system of claim 1, wherein the software is configured to generate an indication of whether it would be profitable to enter into a services agreement with the TPP.

11. The medical management system of claim 10, wherein the indication is generated as a function of at least one payment pattern of the TPP.

12. The medical management system of claim 1, wherein the indication is generated as a function of at least one payment pattern of the TPP with which the patient is associated.

13. The medical management system of claim 1, wherein the software is configured to generate a recommended duration for a primary medical personnel to visit with the patient, the recommended duration being based at least in part upon the historical payment patterns of the TPP to the one or more medical service providers.

14. The medical management system of claim 13, wherein the software is further configured to generate a timer indicating time remaining in the recommended duration.

15. The medical management system of claim 1, further comprising a central controller in communication with the at least one electronic device, the central controller enabling communication between a plurality of electronic devices and databases.

16. The medical management system of claim 15, wherein each of the at least one electronic device is configured as one of a local access terminal, a remote access terminal, a wireless access terminal, and a wireless interface.

17. The medical management system of claim 1, wherein the at least one electronic device is configured as one of a wireless access terminal and a wireless interface, and the at least one electronic device further comprises software configured to receive an electronic superbill and automatically send related charges to a TPP for payment.

18. The medical management system of claim 1, wherein the at least one electronic device is configured as one of a wireless access terminal and a wireless interface, and the at least one electronic device further comprises software configured to transmit to a pharmacy a prescription, billing information and an address to which the prescription should be delivered.

19. The medical management system of claim 1, the at least one electronic device further comprising software configured to evaluate a use pattern of at least one supply of a medical services provider, evaluate an inventory quantity of the at least one supply, evaluate an estimated scheduled appointment use of the at least one supply, and automatically order an appropriate quantity of the at least one supply.

20. The medical management system of claim 1, the at least one electronic device further comprising a biometric identifying device operatively coupled thereto.

21. A medical management system comprising at least one electronic device having:
a) a display;
b) a memory; and
c) a processor operating in accordance with software for:
1) receiving an identifier associated with a third party payor ("TPP") as input;
2) accessing data indicative of the historical payment patterns of the TPP to one or more medical service providers from which a net present value of a future payment by the TPP for at least one requested medical service for a patient associated with the TPP may be generated and assigning a rank to a patient's TPP;
3) generating an indication of the net present value of the at least one requested medical service prior to providing the medical service, the indication based at least in part upon the historical payment patterns of the TPP to the one or more medical service providers; and
4) generating an indication of when the patient is accepted as a new patient based in part on the net present value and the rank assigned to the patient's TPP;
5) generating an indication of when the patient's requested appointment should be scheduled based in part on the net present value and the rank assigned to the patient's TPP, wherein the software is configured to generate recommended duration for a primary medical personnel to visit with the patient, the recommended duration being based in part upon the historical payment patterns of the TPP to the one or more requested medical services and the rank assigned to the patient's TPP.

* * * * *